United States Patent
Yen

(10) Patent No.: US 6,462,177 B1
(45) Date of Patent: Oct. 8, 2002

(54) MAMMALIAN BLOOD LOSS-INDUCED GENE, KD312

(75) Inventor: Kwang-Mu Yen, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/053,374

(22) Filed: Mar. 31, 1998

(51) Int. Cl.⁷ .................. C07K 14/435; C07K 14/47; C12N 9/12

(52) U.S. Cl. .................. 530/350; 435/193; 435/194

(58) Field of Search .................. 530/350; 435/194, 435/193

(56) References Cited

U.S. PATENT DOCUMENTS 5,705,342 A  1/1998  Bischoff et al. ............. 435/6

FOREIGN PATENT DOCUMENTS

WO  WO 97/37020  10/1997

OTHER PUBLICATIONS

Wells. Additivity of mutational effects in proteins. Biochemistry 29(37): 8509–8517, Sep. 18, 1990.*
Bowie et al. Deciphering the message in protein sequences: tolerance to amino acid substitutions. Science 247: 1306–1310, Mar. 16, 1990.*
Petronini et al. Cell susceptibility to apoptosis by glutamine deprivation and rescue:survival and apoptotic death in cultured lymphoma–leukemia cell lines. Journal of cellular physiology 169 (1): 175–185, Oct. 1996.*
The Merck Index, Eighth Edition. Stecher et al, eds. Rahway: Merck & Co. p. 497, 1968.*
Genbank Accession No. AF009246 Kemppainen et al. Jul. 15, 1997.

Kemppainen et al., "Dexamethasone Rapidly Induces a Novel Ras Superfamily Member–related Gene in AtT–20 Cells," Journal of Biological Chemistry, vol. 273, No. 6, pp. 3129–3131 (1998).
Askew et al., "Constitutive c–myc expression in an IL–3–dependent myeloid cell line suppresses cell cycle arrest and accelerates apoptosis," Oncogene, vol. 6, pp. 1915–1922 (1991).
Avruch et al., "Raf meets Ras: Completing the Framework of a Signal Transduction Pathway," TIBS 19, pp. 279–283 Jul. 1994.
Beg et al., "An Essential Role for $NF-_{\kappa}B$ in Preventing $TNF-\alpha$–Induced Cell Death," Science, vol. 274, pp. 782–784 (1996).
Boise et al., "bcl–x, a blc–2–Related Gene That Functions as a Dominant Regulator of Apoptotic Cell Death," Cell, vol. 74, pp. 597–608 (1993).
Capon et al., "Complete Nucleotide Sequences of the T24 Human Bladder Carcinoma Oncogene and its Normal Homologue", Nature, vol. 302, pp. 33–37 (1983).
Carson et al., "Cancer Progression and p53," The Lancet, vol. 346, pp. 1009–1011 (1995).
Evan et al., "Induction of Apoptosis in Fibroblasts by c–myc Protein," Cell, vol. 69, pp. 119–128 (1992).
Fernandez–Sarabla et al., "Bcl–2 Associates with the ras–related Protein R–ras p23," Nature, vol. 366, pp. 274–275 (1993).
Garcia et al., "Prevention of Programmed Cell Death of Sympathetic Neurons by the bcl–2 Proto–Oncogene," Science, vol. 258, pp. 302–304 (1992).

(List continued on next page.)

*Primary Examiner*—Gabrielle Bugaisky
(74) *Attorney, Agent, or Firm*—Robert R. Cook; Stuart L. Watt; Ron K. Levy

(57) ABSTRACT

Disclosed are nucleic acids encoding novel proteins, designated kd312. Also disclosed are amino acid sequences for kd312 polypeptides, methods for preparing kd312 polypeptides, and other related aspects.

6 Claims, 16 Drawing Sheets

```
Human KD312   1 MKLAAMIKKMCPDSDELSIPAKNCYRMVILGSSKVGKTAIVSRFLTGRFE
                ||||||||||||||||||||||||||||||||||||||||||||||||||
Rat KD312     1 MKLAAMIKKMCPDSDELSIPAKNCYRMVILGSSKVGKTAIVSRFLTGRFE 51 DAYTPTIEDFHRKFYSIRGEVYQLDILDTSGNHPFPAMRRLSILTGDVFI
                ||||||||||||||||||||||||||||||||||||||||||||||||||
             51 DAYTPTIEDFHRKFYSIRGEVYQLDILDTSGNHPFPAMRRLSILTGDVFI 101 LVFSLDNRDSFEEVQRLRQQILDTKSCLKNKTKENVDVPLVICGNKGDRD
                ||||||||||||||||:|||||||||||||||||||||||||||||||||
            101 LVFSLDNRDSFEEVQRLKQQILDTKSCLKNKTKENVDVPLVICGNKGDRD 151 FYREVDQREIEQLVGDDPQRCAYFEISAKKNSSLDQMFRALFAMAKLPSE
                |||||:||||||||||||||||||||||||||||||||||||||||||||
            151 FYREVEQREIEQLVGDDPQRCAYFEISAKKNSSLDQMFRALFAMAKLPSE 201 MSPDLHRKVSVQYCDVLHKKALRNKKLLRAGSGGGGGDPGDAFGIVAPFA
                ||||||||||||||||||||||||||||||| |||||.||||||:|||
            201 MSPDLHRKVSVQYCDVLHKKALRNKKLLRAGS.GGGGDHGDAFGILAPFA 251 RRPSVHSDLMYIREKASAGSQAKDKERCVIS 281
                |||||||||||||||.|.:|||||||||||
            250 RRPSVHSDLMYIREKTSVSSQAKDKERCVIS 280
```

OTHER PUBLICATIONS

Graeber et al., "Hypoxia–mediated Selection of Cells with Diminished Apoptotic Potential in Solid Tumours," Nature, vol. 379, pp. 88–91 (1996).

Gruber et al., "Subtractive cDNA Hydridization Using the Multifunctional Plasmid Vester pSPORT 2," Focus 15, No. 3, pp. 59–65 (1993).

Hengartner et al., "C. elegans Cell Survival Gene ced–9 Encodes a Functional Homolog of the Mammalian Proto–Oncogene bcl–2," Cell, vol. 76, pp. 665–676 (1994).

Henkart, "ICE Family Proteases: Mediators of All Apoptotic Cell Death?" Immunity, vol. 4, pp. 195–201 (1996).

Hsu et al., "The TNF Receptor 1–Associated Protein TRADD Signals Cell Death and $NF_{\kappa}B$ Activation," Cell, vol. 81, pp. 495–504 (1995).

Kluck et al., "The Release of Cytochrome c from Mitochondria: A Primary Site for Bcl–2 Regulation of Apoptosis," Science, vol. 275, pp. 1132–1136 (1997).

Kostic et al., "Bcl–2: Prolonging Life in a Transgenic Mouse Model of Familial Amyotrophic Lateral Sclerosis," Science, vol. 277, pp. 559–562 (1997).

Lowe et al., "Structure of the Human and Murine R–ras Genes, Novel Genes Closely Related to ras Proto–oncogenes," Cell, vol. 48, pp. 137–146 (1987).

Miura et al., "Mechanisms of Programmed Cell Death in Caenorhabditis elegans and Vertebrates," Current Topics in Development Biology, vol. 32, pp. 139–174 (1996).

Oltvai et al., "Bcl–2 Heterodimerizes In Vivo with a Conserved Homolog, Bax, That Accelerates Programmed Cell Death," Cell, vol. 74, pp. 609–619, Aug. 1993.

Patterson et al., "Reduced Numatrin/B23/Nucleophosmin Labeling in Apoptotic Jurkat T–lymphoblasts," The Journal of Biological Chemistry, vol. 270, No. 16, pp. 9429–9436 (1995).

Polverino et al., "Selective Activation of Caspases During Apoptotic Induction in HL–60 Cells," The Journal of Biological Chemistry; vol. 272, No. 11, pp. 7013–7021 (1997).

Reed, "Double Identity for Proteins of the Bcl–2 Family," Nature, vol. 387, pp. 773–776, Jun. 1997.

Rudin et al., "Apoptosis and Disease: Regulation and Clinical Relevance of Programmed Cell Death," Annu.Rev.Med. 48:267–81, 1997.

Shimizu et al., "Induction of Apoptosis as well as Necrosis by Hypoxia and Predominant Prevention of Apoptosis by Bcl–2 and Bcl–xL," Cancer Research, 56, pp. 2161–2166 (1996).

Shimizu et al., "Prevention of Hypoxia–Induced Cell Death by Bcl–2 and Bcl–xL," Nature, vol. 374, pp. 811–813 (1995).

Thompson, "Apoptosis in the Pathogenesis and Treatment of Disease," Science, vol. 267, pp. 1456–1462 (1995).

Vaux et al., "Bcl–2 Gene Promotes Haemopoietic Cell Survival and Cooperates with c–myc to Immortalize pre–B Cells," Nature, vol. 335, pp. 440–442 (1988).

Vaux et al., "Prevention of Programmed Cell Death in Caenorhabditis elegans by Human bcl–2," Science, vol. 258, pp. 1955–1957 (1992).

Vaux et al., "The Molecular Biology of Apoptosis," Proc. Natl. Acad. Sci. USA, vol. 93, pp. 2239–2244 (1996).

Vaux, "CED–4–The Third Horseman of Apoptosis," Cell, vol. 90, pp. 389–390 (1997).

Wang et al., "R–Ras Promotes Apoptosis Caused by Growth Factor Deprivation Via a Bcl–2 Suppressible Mechanism," The Journal of Cell Biology, vol. 129, No. 4, pp. 1103–1114 (1995).

Wang et al., "TNF–and Cancer Therapy–Induced Apoptosis: Potentiation by Inhibition of $NF_{\kappa}B$," Science, vol. 274, pp. 784–787 (1996).

Yang, et al., "Bad, a Heterodimeric Partner for $Bcl-x_L$ and Bcl–2, Displaces Bax and Promotes Cell Death," Cell, vol. 80, pp. 285–291, Jan. 1995.

Yang, et al., "Prevention of Apoptosis by Bcl–2: Release of Cytochrome c from Mitochondria Blocked," Science, vol. 275, pp. 1129 (1997).

Zhang et al., "Protein Prenylation: Molecular Mechanisms and Functional Consequences," Annu. Rev. Biochem. 65:241–69 (1996).

Zou et al., "Apaf–1, a Human Protein Homologous to C. elegans CED–4, Participates in Cytochrome c–Dependent Activation of Caspase–3," Cell, vol. 90, pp. 405–413 (1997).

* cited by examiner

FIG. 2

```
Human KD312    1  MKLAAMIKKKMCPSDSELSIPAKNCYRMVILGSSKVGKTAIVSRFLTGRFE
                  ||||||||||||||||||||||||||||||||||||||||||||||||||
Rat KD312      1  MKLAAMIKKKMCPSDSELSIPAKNCYRMVILGSSKVGKTAIVSRFLTGRFE Human KD312   51  DAYTPTIEDFHRKFYSIRGEVYQLDILDTSGNHPFPAMRRLSILTGDVFI
                  ||||||||||||||||||||||||||||||||||||||||||||||||||
Rat KD312     51  DAYTPTIEDFHRKFYSIRGEVYQLDILDTSGNHPFPAMRRLSILTGDVFI Human KD312  101  LVFSLDNRDSFEEVQRLRQQILDTKSCLKNKTKENVDVPLVICGNKGDRD
                  |||||||||||||||| :||||||||||||||||||||||||||||||||
Rat KD312    101  LVFSLDNRDSFEEVQRLKQQILDTKSCLKNKTKENVDVPLVICGNKGDRD Human KD312  151  FYREVDQREIEQLVGDDPQRCAYFEISAKKNSSLDQMFRALFAMAKLPSE
                  |||| :|||||||||||||||||||||||||||||||||||||||||||
Rat KD312    151  FYREVEQREIEQLVGDDPQRCAYFEISAKKNSSLDQMFRALFAMAKLPSE Human KD312  201  MSPDLHRKVSVQYCDVLHKKALRNKKLLRAGSGGGGDPGDAFGIVAPFA
                  |||||||||||||||||||||||||| |||||||| ·|·||||| :||
Rat KD312    201  MSPDLHRKVSVQYCDVLHKKALRNKKLLRAGS.GGGGDHGDAFGILAPFA Human KD312  251  RRPSVHSDLMYIREKASAGSQAKDKERCVIS  281
                  |||||||||||||||· |·|·||||||||||
Rat KD312    250  RRPSVHSDLMYIREKTSVSSQAKDKERCVIS  280
```

FIG. 3

```
Human KD312    4 AAMIKKMCPSDSELSIPAKNCYRMVILGSSKVGKTAIVSRFLTGRFEDAY
                 .:. ..........:: |:|::.::|::||.|:..|:.|:..|:..
Human R-Ras    9 TGRGRPRGGGPGPGDPPPSETHKLVVVGGGGVGKSALTIQFIQSYFVSDY 54 TPTIEDFHRKFYSIRGEVYQLDILDTSGNHPFPAMRRLSILTGDVFILVF
                 ||||.||.|||||:|:..|.:|||||| |.|.|..|||||:||||.|||
              59 DPTIEDSYTKICSVDGIPARLDILDTAGQEEFGAMREQYMRAGHGFLLVF 104 SLDNRDSFEEVQRLRQQILDTKSCLKNKTKENVDVPLVICGNKGDRDFYR
                 ..:|..:.|.:.|.|:.|||..:|..        ..:.|:||||:|.||
             109 AINDRQSFNEVGKLFTQIL........RVKDRDDFPVVLVGNKADLESQR 154 EVDQREIEQLVGDDPQRCAYFEISAK....KNSSLDQMFRAL..FAMAKL
                 :|..:.|.. .:  ::.:|:. |           ..:::||.  ||.:|
             151 QVPRSEASAF..GASHHVAYFEASAKLRLNVDEAFEQLVRAVRKYQEQEL 198 PSEMSPDLHRKVSVQYCDVL 217
                 |.:..||.|||:.::|.: |
             199 PPSPPSAPRKKGGGCPCVLL 218
```

FIG. 5A

| | | |
|---|---|---|
| 1 | TCCGCGCCTGAGGCCCTGAAACCCCGAGTCCGCCCGGCGGTCGCCTCCCGGGAACAAGAG | 60 |
| 61 | CCCGGCTGGGGACCGGAGCGGAAGGGGGCTGGGGCTGGGGCTGTGCTCTGAGGACTGCAA | 120 |
| 121 | TATACGGTCCGCGCATGCACTCAGCAAACGCTGCTGCGCTTACTGGGTTACTTACTAGAT | 180 |
| 181 | TCCTATTCTCTGGGGAAACTGAGAACCAAAGAAAATAAGAGTACGCGCGCGGGAGGTGCA | 240 |
| 241 | GGAATGGGGGTCCTTGCCCGAAGTCGCAGAGGGACAGGGGCACCGCCGGGACCAGAACCC | 300 |
| 301 | CGACGCCCCTGCGGCCGCCGAGCCCGCGGCAGTGGAAAAGCGGAGTCCGAGCGCCTCCAG | 360 |
| 361 | CCTCAGCCCGACCCTGGACTGCTCCCCCAGCCCCGCGCCCAGAGAGCAGGAGCCCGGC | 420 |
| 421 | AGCGGGTGACGAGGTCGCCGGGACTGGGAGCCGGTGCGGGGAGGCGGGCCCCGCGGGGC | 480 |
| 481 | GTGACGCACCGAGCTGGGAGGGCCGGGGCGGGGAGCCGAGCAGGCTGCATATAAGGGCG | 540 |
| 541 | GCGGCCGGGCGCCAAAGCCAGAGCAAGCGGCCTGTGCCCAGATCCTGGGAGAACCCCAGC | 600 |
| 601 | CGAGCCCAGCCTAGCCCGAGCCCAGCCCGAGCGAAGCCGGAGCCCCAAGCCCGAGCCGCG | 660 |
| 661 | CCCAGCCCGAGCAGAGCCCTCCAGCCGCTCACCCCGCGTGCCACCCCAGCGACCCTCAGC | 720 |
| 721 | CGCTCTCTGCCCTTCTCTCGGCCCCGCGCCCGCCCTCGCGGCCCCTCTGCCCAATGAAAC<br>                                                                                    MetLysL | 780 |
| 781 | TGGCCGCGATGATCAAGAAGATGTGCCCGAGCGACTCGGAGCTGAGTATCCCGGCCAAGA<br>euAlaAlaMetIleLysLysMetCysProSerAspSerGluLeuSerIleProAlaLysA | 840 |
| 841 | ACTGCTATCGCATGGTCATCCTCGGCTCGTCCAAGGTGGGCAAGACGGCCATCGTGTCGC<br>snCysTyrArgMetValIleLeuGlySerSerLysValGlyLysThrAlaIleValSerA | 900 |
| 901 | GCTTCCTCACCGGCCGCTTCGAGGACGCCTACACGCCTACCATCGAGGACTTCCACCGCA<br>rgPheLeuThrGlyArgPheGluAspAlaTyrThrProThrIleGluAspPheHisArgL | 960 |
| 961 | AGTTCTACTCCATCCGCGGCGAGGTCTACCAGCTCGACATCCTCGACACGTCCGGCAACC<br>ysPheTyrSerIleArgGlyGluValTyrGlnLeuAspIleLeuAspThrSerGlyAsnH | 1020 |
| 1021 | ACCCGTTCCCCGCCATGCGGCGCCTCTCCATCCTCACAGGTGAGCCGGGGGCCGGGCAGG<br>isProPheProAlaMetArgArgLeuSerIleLeuThrG | 1080 |

FIG.5B

| | | |
|---|---|---|
| 1081 | TGCGGGAGGGAAGGGCGGGGAACCCTCGGCCAGGGCGCCCCGCGAGCGCCGGTCCGGCTG | 1140 |
| 1141 | CTGCGCGCCGAGTAGTGCGCTTCGCGCTTAGAGAGGCTAGCGCGCCCCGCGCGGCCTCAA | 1200 |
| 1201 | AGTCAGCCCGACTTGTCCCTGGGCGGCCACCCTCACCTTCTCCTTTTCTGCTCTCTGTG | 1260 |
| 1261 | CCCCCTCTAGGAGACGTTTTCATCCTGGTGTTCAGTCTGGACAACCGCGACTCCTTCGAG<br>               lyAspValPheIleLeuValPheSerLeuAspAsnArgAspSerPheGlu | 1320 |
| 1321 | GAGGTGCAGCGGCTCAGGCAGCAGATCCTCGACACCAAGTCTTGCCTCAAGAACAAAACC<br>GluValGlnArgLeuArgGlnGlnIleLeuAspThrLysSerCysLeuLysAsnLysThr | 1380 |
| 1381 | AAGGAGAACGTGGACGTGCCCCTGGTCATCTGCGGCAACAAGGGTGACCGCGACTTCTAC<br>LysGluAsnValAspValProLeuValIleCysGlyAsnLysGlyAspArgAspPheTyr | 1440 |
| 1441 | CGCGAGGTGGACCAGCGCGAGATCGAGCAGCTGGTGGGCGACGACCCCCAGCGCTGCGCC<br>ArgGluValAspGlnArgGluIleGluGlnLeuValGlyAspAspProGlnArgCysAla | 1500 |
| 1501 | TACTTCGAGATCTCGGCCAAGAAGAACAGCAGCCTGGACCAGATGTTCCGCGCGCTCTTC<br>TyrPheGluIleSerAlaLysLysAsnSerSerLeuAspGlnMetPheArgAlaLeuPhe | 1560 |
| 1561 | GCCATGGCCAAGCTGCCCAGCGAGATGAGCCCAGACCTGCACCGCAAGGTCTCGGTGCAG<br>AlaMetAlaLysLeuProSerGluMetSerProAspLeuHisArgLysValSerValGln | 1620 |
| 1621 | TACTGCGACGTGCTGCACAAGAAGGCGCTGCGGAACAAGAAGCTGCTGCGGGCCGGCAGC<br>TyrCysAspValLeuHisLysLysAlaLeuArgAsnLysLysLeuLeuArgAlaGlySer | 1680 |
| 1681 | GGCGGCGGCGGCGGCGACCCGGGCGACGCCTTTGGCATCGTGGCACCCTTCGCGCGCCGG<br>GlyGlyGlyGlyGlyAspProGlyAspAlaPheGlyIleValAlaProPheAlaArgArg | 1740 |
| 1741 | CCCAGCGTACACAGCGACCTCATGTACATCCGCGAGAAGGCCAGCGCCGGCAGCCAGGCC<br>ProSerValHisSerAspLeuMetTyrIleArgGluLysAlaSerAlaGlySerGlnAla | 1800 |
| 1801 | AAGGACAAGGAGCGCTGCGTCATCAGCTAGGAGCCCCGCCGCTGGCGACACAACCTAA<br>LysAspLysGluArgCysValIleSerEnd | 1860 |
| 1861 | GGAGGACCTTTTTGTTAAGTCAAATCCAACGGCCCGGTGCGCCCCAGGCCGGGAGCGCGC | 1920 |
| 1921 | GCGGACTGGCGTCTCCCCTCCCGGCGATCCGCCCCCAGCACTGGGGAGGCGCCACTGAAC | 1980 |
| 1981 | CGAGAAGGGATGGTCATCTGCTCCGGAAGGAAAGAGAACGGGCCAAGACTGGGACTATTC | 2040 |

FIG.6

```
         -117                                                          -65
P-Epo    CCTGCTCTGACCCCCGGGGTGGCCCCTACCCCCTGGCGACCCCTCACGCACACAGC
              |||||||||||   |||||||||  ||       ||||||||||
5'-kd312      CGCTCACCCCCGGGGTGCCACC---CCCTGGGCGGCCCCTC
              120              139 187              201
```

FIG.7A

| | | |
|---|---|---|
| 1 | CCAGCGCACGTAGGTCTGGAGCACAGCCTCAGGCTCCAAGGCGGAGGTCACTGCGTCTAG | 60 |
| 61 | GAGGAGCCCGGAGCGTCCGGGGGCGGGACGTGACGCACCTTGGCTGGGAGGTGCCAGCCC | 120 |
| 121 | AGGCTTCGGTCAGCTGCA<u>TATAA</u>GAGTGGTGTGAGGCGCGGAAAGCCTGAGCCCGCTGCC | 180 |
| 181 | TGTACTCAAGATTCCAGGCCAGCTCGCGCGGTCCCGAAGCCAAACTCTTCCACCACTCCG | 240 |
| 241 | GCGCCCTCTGCAGCCCTCTACCTTCTCTCAGCCACGCATCTGCCCTGGGGCCCCTCTGCC | 300 |
| 301 | CAATGAAACTGGCCGCGATGATCAAGAAGATGTGCCCAAGCGACTCTGAACTGAGTATCC<br>　　　MetLysLeuAlaAlaMetIleLysLysMetCysProSerAspSerGluLeuSerIleP | 360 |
| 361 | CGGCCAAGAACTGCTACAGGATGGTCATCCTCGGCTCATCCAAAGTGGGCAAGACGGCCA<br>roAlaLysAsnCysTyrArgMetValIleLeuGlySerSerLysValGlyLysThrAlaI | 420 |
| 421 | TCGTGTCGCGCTTCCTCACGGGCCGCTTCGAGGACGCTTACACCCCTACCATTGAAGACT<br>leValSerArgPheLeuThrGlyArgPheGluAspAlaTyrThrProThrIleGluAspP | 480 |
| 481 | TCCACCGAAAGTTTTACTCGATCCGCGGCGAAGTCTACCAGTTGGACATACTGGACACAT<br>heHisArgLysPheTyrSerIleArgGlyGluValTyrGlnLeuAspIleLeuAspThrS | 540 |
| 541 | CTGGCAATCATCCGTTTCCCGCCATGCGGCGCCTCTCTATCCTCACAGGTGAGTGGGGGA<br>erGlyAsnHisProPheProAlaMetArgArgLeuSerIleLeuThrG | 600 |
| 601 | CCGACAGGGACCGTGGGGAGGGAATCTGCGGGGAGCGGATGGGGCGGTGTGTTGTGCTTG | 660 |
| 661 | GGGCTGTGCTGTCTGCTGCTCCGTGCTTGGCAGCTGCCCTCACCTTTCCACTCGTTCCCT | 720 |
| 721 | TGTAGGAGACGTTTTCATTCTGGTGTTCAGCTTAGACAACCGCGACTCCTTCGAGGAGGT<br>　　　　lyAspValPheIleLeuValPheSerLeuAspAsnArgAspSerPheGluGluVa | 780 |
| 781 | GCAAAGGCTCAAACAGCAGATCCTAGACACCAAGTCCTGTCTCAAGAACAAAACCAAAGA<br>lGlnArgLeuLysGlnGlnIleLeuAspThrLysSerCysLeuLysAsnLysThrLysGl | 840 |
| 841 | GAATGTGGACGTGCCGCTGGTCATTTGCGGTAACAAAGGGGACCGGGACTTCTACCGCGA<br>uAsnValAspValProLeuValIleCysGlyAsnLysGlyAspArgAspPheTyrArgGl | 900 |
| 901 | AGTGGAGCAGCGGGAGATTGAGCAGCTGGTGGGCGATGACCCTCAGCGTTGTGCCTACTT<br>uValGluGlnArgGluIleGluGlnLeuValGlyAspAspProGlnArgCysAlaTyrPh | 960 |

FIG. 7B

| | | |
|---|---|---|
| 961 | CGAGATCTCGGCCAAGAAGAATAGCAGCCTGGACCAGATGTTCCGTGCGCTCTTTGCCAT | 1020 |
| | eGluIleSerAlaLysLysAsnSerSerLeuAspGlnMetPheArgAlaLeuPheAlaMe | |
| 1021 | GGCCAAGCTGCCTAGCGAGATGAGCCCTGACTTGCACCGCAAGGTGTCTGTGCAGTACTG | 1080 |
| | tAlaLysLeuProSerGluMetSerProAspLeuHisArgLysValSerValGlnTyrCy | |
| 1081 | TGACGTGCTGCACAAAAAGGCTCTGAGGAACAAGAAGCTTCTGCGTGCGGGCAGCGGAGG | 1140 |
| | sAspValLeuHisLysLysAlaLeuArgAsnLysLysLeuLeuArgAlaGlySerGlyGl | |
| 1141 | TGGGGGCGACCACGGAGATGCCTTTGGCATCTTGGCGCCCTTTGCTCGCAGACCTAGCGT | 1200 |
| | yGlyGlyAspHisGlyAspAlaPheGlyIleLeuAlaProPheAlaArgArgProSerVa | |
| 1201 | GCATAGCGACCTCATGTACATTCGTGAGAAAACCAGTGTCAGCAGCCAGGCTAAGGACAA | 1260 |
| | lHisSerAspLeuMetTyrIleArgGluLysThrSerValSerSerGlnAlaLysAspLy | |
| 1261 | GGAGCGCTGTGTCATCAGTTAGGAGCCCCCAGGGTCAGTCAGCCACACAACCTGAGGACC | 1320 |
| | sGluArgCysValIleSerEnd | |
| 1321 | TTTTTTGTTCAAAAGTCAAATCGGTTTCCCAGGCTAACCTGTGCACTCCGTGCCCCAAGA | 1380 |
| 1381 | GCGCCAGCTGGCCTCCTCCCTCCCTCCCTGAGACCCAGCCCTGTGCACCAGGGAGATGCT | 1440 |
| 1441 | GCCAAGACAGTAAGGGACAGTCATCTGCTGTGAGAGGAAAGAACTAGCTAAGACTGGGAC | 1500 |
| 1501 | TTTCGCCTCCGATTCTGGGATGCCAGGACCCAGCAGAGGGTTAGTTGGCGTTTTTCTCAG | 1560 |
| 1561 | AGACTTTGAGAGTGTGTGAAGGGCTTCGGCCTCTGAGACTTCAAGTAACTGTGCGGCTTG | 1620 |
| 1621 | CTGTGGGGCCAGGACTAACAGGGCATTATCTCGTCTGTGATTGGTGTTGCCATGACTGCT | 1680 |
| 1681 | GTCAGCCACCTCTGTCCTCAGCAAACTGGAAACTTTGGCTCGAGGTGGGGGTTCAATCAT | 1740 |
| 1741 | AGCCAGACAACTTGTTTACATGTGTGTGTGTGTAATTACCCAAAAGGAAAACAAAACA | 1800 |
| 1801 | CAAAACTTGCACTTTAATAGTTCCAGTGTCAACGTGACATGAACAAAATCTCTACATTTC | 1860 |
| 1861 | TATTGTGTGAGGTCTTTATTATTTTTTTAATTTAAAATAAAATAATTTTAAAATGGAAA | 1920 |
| 1921 | ATGGTGCTTCGCTTTGCTTTTGCTTTTAGGCTTCCTGCCTCGGTGGCAGTGGCCAAGAAC | 1980 |
| 1981 | TGGAAAAGGACCTGGCTTTCAGAATATGGTCTCCCACTTCCAAGTGGGACCTTCTGGCTT | 2040 |

FIG. 8A

```
  1  ACGCCTGCAGGTACCGGTCCGGAATTCCCGGGTCGACCACGCGTCCGGCGGCCTGTGCCC    60

61  AGATCCTGGGAGAACCCCAGCCGAGCCCAGCCTAGCCCGAGCCCAGCCCGAGCGAAGCCG   120

121  GAGCCCCAAGCCCGAGCCGCGCCCAGCCCGAGCAGAGCCCTCCAGCCGCTCACCCCGCGT   180

181  GCCACCCCAGCGACCCTCAGCCGCTCTCTGCCCTTCTCTCGGCCCCGCGCCCGCCCTCGC   240

241  GGCCCCTCTGCCCAATGAAACTGGCCGCGATGATCAAGAAGATGTGCCCGAGCGACTCGG   300
                   MetLysLeuAlaAlaMetIleLysLysMetCysProSerAspSerG

301  AGCTGAGTATCCCGGCCAAGAACTGCTATCGCATGGTCATCCTCGGCTCGTCCAAGGTGG   360
     luLeuSerIleProAlaLysAsnCysTyrArgMetValIleLeuGlySerSerLysValG

361  GCAAGACGGCCATCGTGTCGCGCTTCCTCACCGGCCGCTTCGAGGACGCCTACACGCCTA   420
     lyLysThrAlaIleValSerArgPheLeuThrGlyArgPheGluAspAlaTyrThrProT

421  CCATCGAGGACTTCCACCGCAAGTTCTACTCCATCCGCGGCGAGGTCTACCAGCTCGACA   480
     hrIleGluAspPheHisArgLysPheTyrSerIleArgGlyGluValTyrGlnLeuAspI

481  TCCTCGACACGTCCGGCAACCACCCGTTCCCCGCCATGCGGCGCCTCTCCATCCTCACAG   540
     leLeuAspThrSerGlyAsnHisProPheProAlaMetArgArgLeuSerIleLeuThrG

541  GAGACGTTTTCATCCTGGTGTTCAGTCTGGACAACCGCGACTCCTTCGAGGAGGTGCAGC   600
     lyAspValPheIleLeuValPheSerLeuAspAsnArgAspSerPheGluGluValGlnA

601  GGCTCAGGCAGCAGATCCTCGACACCAAGTCTTGCCTCAAGAACAAAACCAAGGAGAACG   660
     rgLeuArgGlnGlnIleLeuAspThrLysSerCysLeuLysAsnLysThrLysGluAsnV

661  TGGACGTGCCCCTGGTCATCTGCGGCAACAAGGGTGACCGCGACTTCTACCGCGAGGTGG   720
     alAspValProLeuValIleCysGlyAsnLysGlyAspArgAspPheTyrArgGluValA

721  ACCAGCGCGAGATCGAGCAGCTGGTGGGCGACGACCCCCAGCGCTGCGCCTACTTCGAGA   780
     spGlnArgGluIleGluGlnLeuValGlyAspAspProGlnArgCysAlaTyrPheGluI

781  TCTCGGCCAAGAAGAACAGCAGCCTGGACCAGATGTTCCGCGCGCTCTTCGCCATGGCCA   840
     leSerAlaLysLysAsnSerSerLeuAspGlnMetPheArgAlaLeuPheAlaMetAlaL
```

FIG.8B

```
 841  AGCTGCCCAGCGAGATGAGCCCAGACCTGCACCGCAAGGTCTCGGTGCAGTACTGCGACG   900
      ysLeuProSerGluMetSerProAspLeuHisArgLysValSerValGlnTyrCysAspV

901  TGCTGCACAAGAAGGCGCTGCGGAACAAGAAGCTGCTGCGGGCCGGCAGCGGCGGCGGCG   960
      alLeuHisLysLysAlaLeuArgAsnLysLysLeuLeuArgAlaGlySerGlyGlyGlyG

961  GCGGCGACCCGGGCGACGCCTTTGGCATCGTGGCACCCTTCGCGCGCCGGCCCAGCGTAC  1020
      lyGlyAspProGlyAspAlaPheGlyIleValAlaProPheAlaArgArgProSerValH

1021  ACAGCGACCTCATGTACATCCGCGAGAAGGCCAGCGCCGGCAGCCAGGCCAAGGACAAGG  1080
      isSerAspLeuMetTyrIleArgGluLysAlaSerAlaGlySerGlnAlaLysAspLysG

1081  AGCGCTGCGTCATCAGCTAGGAGCCCCGCCGCGCTGGCGACACAACCTAAGGAGGACCTT  1140
      luArgCysValIleSerEnd

1141  TTTGTTAAGTCAAATCCAACGGCCCGGTGCGCCCCAGGCCGGGAGCGCGCGCGGACTGGC  1200

1201  GTCTCCCCTCCCGGCGATCCGCCCCCAGCACTGGGGAGGCGCCACTGAACCGAGAAGGGA  1260

1261  TGGTCATCTGCTCCGGAAGGAAAGAGAACGGGCCAAGACTGGGACTATTCCCCACCCCCG  1320

1321  GTCCCCATTGAGGCCCGCCACCCCCATAACTTTGGGAGCGAGGGCCCAGCCGAGGGTGGA  1380

1381  TTTATCTTCTCAAAGACCTAAGAGTGAGCGCGGGGTGGGGAGGGATGTGAAGTTATCCA  1440

1441  GCCTCTGCTAGGCTTCAAGAAACCGTCATGCCCGCTTGAGGGTCAGGACCCACGGGGCAT  1500

1501  TATCTTGTCTGTGATTCCGGGTTGCTGTGACAGCCGGTAGAGCCTCTGCCCTCCCGAAAC  1560

1561  TAAGCGGGGGGCGTGGGTCAAATCATAGCCAAGTGACTTGTTTACATGTGAGTGAAACT  1620

1621  GCACAAAGGAACACAAAACAAAACTTGCACTTTAACGGTAGTTCCGGTGTCAACATGGAC  1680

1681  ACGAACAAAACCTTACCCAGGTGTTTATACTGTGTGTGTGTGAGGTCTTTAAAGTTATTG  1740

1741  CTTTATTTGGTTTTTTAATATACAATAAATAATTTAAAATGGAAAAAAAAAAAAAAAGG  1800

1801  GCGGCCGCTCTAGAGGATCCCTCGAGGGCCCAAGCTTACGC   1841
```

FIG.9A

```
  1  CCCGCTGCCTGTACTCAAGATTCCAGGCCAGCTCGCGCGGTCCCGAAGCCAAACTCTTCC    60

61  ACCACTCCGGCGCCCTCTGCAGCCCTCTACCTTCTCTCAGCCACGCATCTGCCCTGGGGC   120

121  CCCTCTGCCCAATGAAACTGGCCGCGATGATCAAGAAGATGTGCCCAAGCGACTCTGAAC   180
                MetLysLeuAlaAlaMetIleLysLysMetCysProSerAspSerGluL

181  TGAGTATCCCGGCCAAGAACTGCTACAGGATGGTCATCCTCGGCTCATCCAAAGTGGGCA   240
     euSerIleProAlaLysAsnCysTyrArgMetValIleLeuGlySerSerLysValGlyL

241  AGACGGCCATCGTGTCGCGCTTCCTCACGGGCCGCTTCGAGGACGCTTACACCCCTACCA   300
     ysThrAlaIleValSerArgPheLeuThrGlyArgPheGluAspAlaTyrThrProThrI

301  TTGAAGACTTCCACCGAAAGTTTTACTCGATCCGCGGCGAAGTCTACCAGTTGGACATAC   360
     leGluAspPheHisArgLysPheTyrSerIleArgGlyGluValTyrGlnLeuAspIleL

361  TGGACACATCTGGCAATCATCCGTTTCCCGCCATGCGGCGCCTCTCTATCCTCACAGGAG   420
     euAspThrSerGlyAsnHisProPheProAlaMetArgArgLeuSerIleLeuThrGlyA

421  ACGTTTTCATTCTGGTGTTCAGCTTAGACAACCGCGACTCCTTCGAGGAGGTGCAAAGGC   480
     spValPheIleLeuValPheSerLeuAspAsnArgAspSerPheGluGluValGlnArgL

481  TCAAACAGCAGATCCTAGACACCAAGTCCTGTCTCAAGAACAAAACCAAAGAGAATGTGG   540
     euLysGlnGlnIleLeuAspThrLysSerCysLeuLysAsnLysThrLysGluAsnValA

541  ACGTGCCGCTGGTCATTTGCGGTAACAAAGGGGACCGGGACTTCTACCGCGAAGTGGAGC   600
     spValProLeuValIleCysGlyAsnLysGlyAspArgAspPheTyrArgGluValGluG

601  AGCGGGAGATTGAGCAGCTGGTGGGCGATGACCCTCAGCGTTGTGCCTACTTCGAGATCT   660
     lnArgGluIleGluGlnLeuValGlyAspAspProGlnArgCysAlaTyrPheGluIleS

661  CGGCCAAGAAGAATAGCAGCCTGGACCAGATGTTCCGTGCGCTCTTTGCCATGGCCAAGC   720
     erAlaLysLysAsnSerSerLeuAspGlnMetPheArgAlaLeuPheAlaMetAlaLysL

721  TGCCTAGCGAGATGAGCCCTGACTTGCACCGCAAGGTGTCTGTGCAGTACTGTGACGTGC   780
     euProSerGluMetSerProAspLeuHisArgLysValSerValGlnTyrCysAspValL

781  TGCACAAAAAGGCTCTGAGGAACAAGAAGCTTCTGCGTGCGGGCAGCGGAGGTGGGGGCG   840
     euHisLysLysAlaLeuArgAsnLysLysLeuLeuArgAlaGlySerGlyGlyGlyGlyA
```

FIG.9B

```
841   ACCACGGAGATGCCTTTGGCATCTTGGCGCCCTTTGCTCGCAGACCTAGCGTGCATAGCG   900
      spHisGlyAspAlaPheGlyIleLeuAlaProPheAlaArgArgProSerValHisSerA

901   ACCTCATGTACATTCGTGAGAAAACCAGTGTCAGCAGCCAGGCTAAGGACAAGGAGCGCT   960
      spLeuMetTyrIleArgGluLysThrSerValSerSerGlnAlaLysAspLysGluArgC

961   GTGTCATCAGTTAGGAGCCCCCAGGGTCAGTCAGCCACACAACCTGAGGACCTTTTTTGT   1020
      ysValIleSerEnd

1021  TCAAAAGTCAAATCGGTTTCCCAGGCTAACCTGTGCACTCCGTGCCCCAAGAGCGCCAGC   1080

1081  TGGCCTCCTCCCTCCCTCCCTGAGACCCAGCCCTGTGCACCAGGGAGATGCTGCCAAGAC   1140

1141  AGTAAGGGACAGTCATCTGCTGTGAGAGGAAAGAACTAGCTAAGACTGGGACTTTCGCCT   1200

1201  CCGATTCTGGGATGCCAGGACCCAGCAGAGGGTTAGTTGGCGTTTTTCTCAGAGACTTTG   1260

1261  AGAGTGTGTGAAGGGCTTCGGCCTCTGAGACTTCAAGTAACTGTGCGGCTTGCTGTGGGG   1320

1321  CCAGGACTAACAGGGCATTATCTCGTCTGTGATTGGTGTTGCCATGACCGCTGTCAGCCA   1380

1381  CCTCTGTCCTCAGCAAACTGGAAACTTTGGCTCGAGGTGGGGGTTCAATCATAGCCAGAC   1440

1441  AACTTGTTTACATGTGTGTGTGTGTAATTACCCAAAAGGAAAACAAAACACAAAACTT    1500

1501  GCACTTTAACAGTTCCAGTGTCAACGTGACATGAACAAAATCTCTACATTTCTATTGTGT   1560

1561  GAGGTCTTTATTATTTTTTTTAATTTAAAATAAAATAATTTTAAAATGGAAAAAAAAAAA   1620

1621  AAAAAAAAAAAAAGGGCGGCCGCTCTAGAGGATCCAAGCTTACGTACGCGTGCATGCGAC   1680

1681  GTCATACTC   1689
```

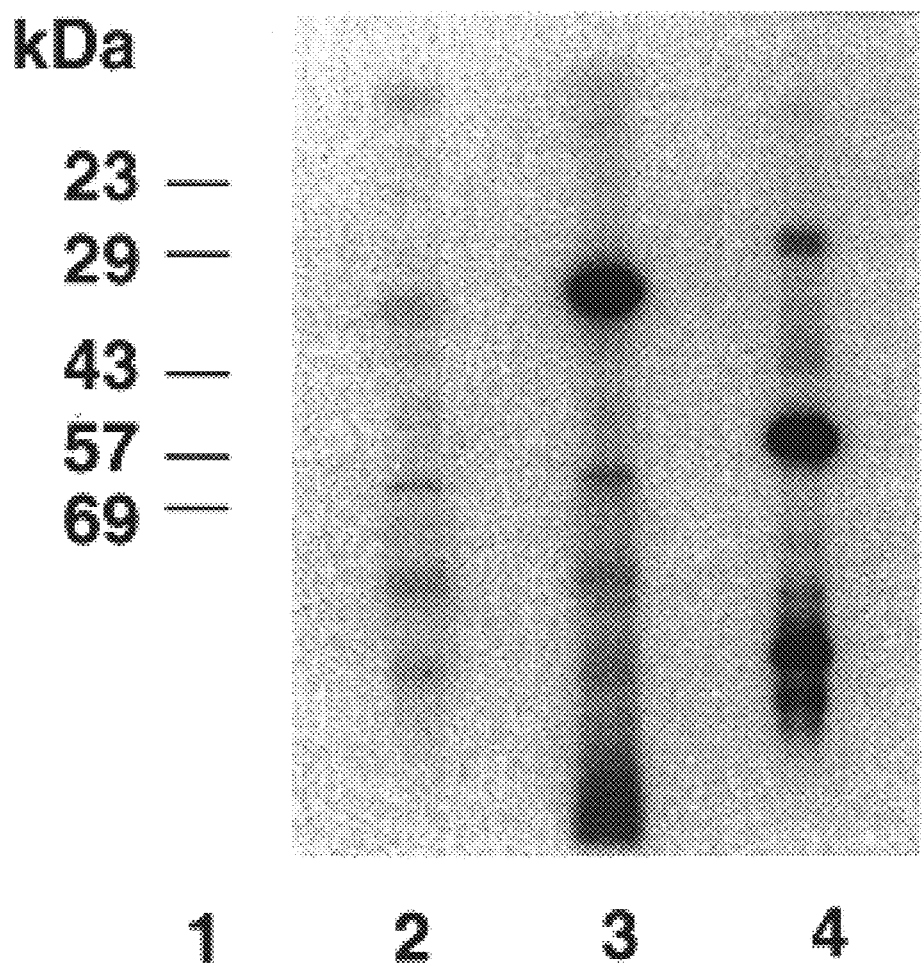

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1841 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 255..1097

(xi) SEQUENCE DESCRIPTION: SEQ ID NO:1:

```
ACGCCTGCAG GTACCGGTCC GGAATTCCCG GGTCGACCAC GCGTCCGGCG GCCTGTGCCC         60

AGATCCTGGG AGAACCCCAG CCGAGCCCAG CCTAGCCCGA GCCCAGCCCG AGCGAAGCCG        120

GAGCCCCAAG CCCGAGCCGC GCCCAGCCCG AGCAGAGCCC TCCAGCCGCT CACCCCGCGT        180

GCCACCCCAG CGACCCTCAG CCGCTCTCTG CCCTTCTCTC GGCCCCGCGC CCGCCCTCGC        240

GGCCCCTCTG CCCA ATG AAA CTG GCC GCG ATG ATC AAG AAG ATG TGC CCG         290
              Met Lys Leu Ala Ala Met Ile Lys Lys Met Cys Pro
                1               5                  10

AGC GAC TCG GAG CTG AGT ATC CCG GCC AAG AAC TGC TAT CGC ATG GTC         338
Ser Asp Ser Glu Leu Ser Ile Pro Ala Lys Asn Cys Tyr Arg Met Val
        15                  20                  25

ATC CTC GGC TCG TCC AAG GTG GGC AAG ACG GCC ATC GTG TCG CGC TTC         386
Ile Leu Gly Ser Ser Lys Val Gly Lys Thr Ala Ile Val Ser Arg Phe
    30                  35                  40

CTC ACC GGC CGC TTC GAG GAC GCC TAC ACG CCT ACC ATC GAG GAC TTC         434
Leu Thr Gly Arg Phe Glu Asp Ala Tyr Thr Pro Thr Ile Glu Asp Phe
45                  50                  55                  60

CAC CGC AAG TTC TAC TCC ATC CGC GGC GAG GTC TAC CAG CTC GAC ATC         482
His Arg Lys Phe Tyr Ser Ile Arg Gly Glu Val Tyr Gln Leu Asp Ile
                65                  70                  75

CTC GAC ACG TCC GGC AAC CAC CCG TTC CCC GCC ATG CGG CGC CTC TCC         530
Leu Asp Thr Ser Gly Asn His Pro Phe Pro Ala Met Arg Arg Leu Ser
            80                  85                  90

ATC CTC ACA GGA GAC GTT TTC ATC CTG GTG TTC AGT CTG GAC AAC CGC         578
Ile Leu Thr Gly Asp Val Phe Ile Leu Val Phe Ser Leu Asp Asn Arg
        95                  100                 105

GAC TCC TTC GAG GAG GTG CAG CGG CTC AGG CAG CAG ATC CTC GAC ACC         626
Asp Ser Phe Glu Glu Val Gln Arg Leu Arg Gln Gln Ile Leu Asp Thr
    110                 115                 120

AAG TCT TGC CTC AAG AAC AAA ACC AAG GAG AAC GTG GAC GTG CCC CTG         674
Lys Ser Cys Leu Lys Asn Lys Thr Lys Glu Asn Val Asp Val Pro Leu
125                 130                 135                 140

GTC ATC TGC GGC AAC AAG GGT GAC CGC GAC TTC TAC CGC GAG GTG GAC         722
Val Ile Cys Gly Asn Lys Gly Asp Arg Asp Phe Tyr Arg Glu Val Asp
                145                 150                 155

CAG CGC GAG ATC GAG CAG CTG GTG GGC GAC GAC CCC CAG CGC TGC GCC         770
Gln Arg Glu Ile Glu Gln Leu Val Gly Asp Asp Pro Gln Arg Cys Ala
            160                 165                 170

TAC TTC GAG ATC TCG GCC AAG AAG AAC AGC AGC CTG GAC CAG ATG TTC         818
Tyr Phe Glu Ile Ser Ala Lys Lys Asn Ser Ser Leu Asp Gln Met Phe
        175                 180                 185
```

```
CGC GCG CTC TTC GCC ATG GCC AAG CTG CCC AGC GAG ATG AGC CCA GAC      866
Arg Ala Leu Phe Ala Met Ala Lys Leu Pro Ser Glu Met Ser Pro Asp
    190                 195                 200

CTG CAC CGC AAG GTC TCG GTG CAG TAC TGC GAC GTG CTG CAC AAG AAG      914
Leu His Arg Lys Val Ser Val Gln Tyr Cys Asp Val Leu His Lys Lys
205                 210                 215                 220

GCG CTG CGG AAC AAG AAG CTG CTG CGG GCC GGC AGC GGC GGC GGC          962
Ala Leu Arg Asn Lys Lys Leu Leu Arg Ala Gly Ser Gly Gly Gly
                    225                 230                 235

GGC GAC CCG GGC GAC GCC TTT GGC ATC GTG GCA CCC TTC GCG CGC CGG     1010
Gly Asp Pro Gly Asp Ala Phe Gly Ile Val Ala Pro Phe Ala Arg Arg
            240                 245                 250

CCC AGC GTA CAC AGC GAC CTC ATG TAC ATC CGC GAG AAG GCC AGC GCC     1058
Pro Ser Val His Ser Asp Leu Met Tyr Ile Arg Glu Lys Ala Ser Ala
        255                 260                 265

GGC AGC CAG GCC AAG GAC AAG GAG CGC TGC GTC ATC AGC TAGGAGCCCC      1107
Gly Ser Gln Ala Lys Asp Lys Glu Arg Cys Val Ile Ser
    270                 275                 280

GCCGCGCTGG CGACACAACC TAAGGAGGAC CTTTTTGTTA AGTCAAATCC AACGGCCCGG   1167

TGCGCCCCAG GCCGGGAGCG CGCGCGGACT GGCGTCTCCC CTCCCGGCGA TCCGCCCCCA   1227

GCACTGGGGA GGCGCCACTG AACCGAGAAG GGATGGTCAT CTGCTCCGGA AGGAAAGAGA   1287

ACGGGCCAAG ACTGGGACTA TTCCCCACCC CCGGTCCCCA TTGAGGCCCG CCACCCCCAT   1347

AACTTTGGGA GCGAGGGCCC AGCCGAGGGT GGATTTATCT TCTCAAAGAC CTAAGAGTGA   1407

GCGCGGGGTG GGGGAGGGAT GTGAAGTTAT CCAGCCTCTG CTAGGCTTCA AGAAACCGTC   1467

ATGCCCGCTT GAGGGTCAGG ACCCACGGGG CATTATCTTG TCTGTGATTC CGGGTTGCTG   1527

TGACAGCCGG TAGAGCCTCT GCCCTCCCGA AACTAAGCGG GGGGGCGTGG GTCAAATCAT   1587

AGCCAAGTGA CTTGTTTACA TGTGAGTGAA ACTGCACAAA GGAACACAAA ACAAAACTTG   1647

CACTTTAACG GTAGTTCCGG TGTCAACATG GACACGAACA AAACCTTACC CAGGTGTTTA   1707

TACTGTGTGT GTGTGAGGTC TTTAAAGTTA TTGCTTTATT TGGTTTTTTA ATATACAATA   1767

AAATAATTTA AAATGGAAAA AAAAAAAAAA AGGGCGGCCG CTCTAGAGGA TCCCTCGAGG   1827

GCCCAAGCTT ACGC                                                    1841

(2) INFORMATION FOR SEQ ID NO:2:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Leu Ala Ala Met Ile Lys Lys Met Cys Pro Ser Asp Ser Glu
1               5                   10                  15

Leu Ser Ile Pro Ala Lys Asn Cys Tyr Arg Met Val Ile Leu Gly Ser
                20                  25                  30

Ser Lys Val Gly Lys Thr Ala Ile Val Ser Arg Phe Leu Thr Gly Arg
            35                  40                  45

Phe Glu Asp Ala Tyr Thr Pro Thr Ile Glu Asp Phe His Arg Lys Phe
        50                  55                  60

Tyr Ser Ile Arg Gly Glu Val Tyr Gln Leu Asp Ile Leu Asp Thr Ser
65                  70                  75                  80

Gly Asn His Pro Phe Pro Ala Met Arg Arg Leu Ser Ile Leu Thr Gly
```

```
                     85                  90                  95
Asp Val Phe Ile Leu Val Phe Ser Leu Asp Asn Arg Asp Ser Phe Glu
                100                 105                 110
Glu Val Gln Arg Leu Arg Gln Gln Ile Leu Asp Thr Lys Ser Cys Leu
        115                 120                 125
Lys Asn Lys Thr Lys Glu Asn Val Asp Val Pro Leu Val Ile Cys Gly
    130                 135                 140
Asn Lys Gly Asp Arg Asp Phe Tyr Arg Glu Val Asp Gln Arg Glu Ile
145                 150                 155                 160
Glu Gln Leu Val Gly Asp Pro Gln Arg Cys Ala Tyr Phe Glu Ile
                165                 170                 175
Ser Ala Lys Lys Asn Ser Ser Leu Asp Gln Met Phe Arg Ala Leu Phe
            180                 185                 190
Ala Met Ala Lys Leu Pro Ser Glu Met Ser Pro Asp Leu His Arg Lys
        195                 200                 205
Val Ser Val Gln Tyr Cys Asp Val Leu His Lys Lys Ala Leu Arg Asn
    210                 215                 220
Lys Lys Leu Leu Arg Ala Gly Ser Gly Gly Gly Gly Asp Pro Gly
225                 230                 235                 240
Asp Ala Phe Gly Ile Val Ala Pro Phe Ala Arg Arg Pro Ser Val His
                245                 250                 255
Ser Asp Leu Met Tyr Ile Arg Glu Lys Ala Ser Ala Gly Ser Gln Ala
            260                 265                 270
Lys Asp Lys Glu Arg Cys Val Ile Ser
        275                 280

(2) INFORMATION FOR SEQ ID NO:3:

(i) SEQUENCE CHARACTERISTICS:
        (A) LENGTH: 3986 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TCCGCGCCTG AGGCCCTGAA ACCCCGAGTC CGCCCGGCGG TCGCCTCCCG GGAACAAGAG      60

CCCGGCTGGG GACCGGAGCG GAAGGGGGCT GGGGCTGGGG CTGTGCTCTG AGGACTGCAA     120

TATACGGTCC GCGCATGCAC TCAGCAAACG CTGCTGCGCT TACTGGGTTA CTTACTAGAT     180

TCCTATTCTC TGGGGAAACT GAGAACCAAA GAAAATAAGA GTACGCGCGC GGGAGGTGCA     240

GGAATGGGGG TCCTTGCCCG AAGTCGCAGA GGGACAGGGG CACCGCCGGG ACCAGAACCC     300

CGACGCCCCT GCGGCCGCCG AGCCCGCGGC AGTGGAAAAG CGGAGTCCGA GCGCCTCCAG     360

CCTCAGCCCG ACCCTGGACT GCTCCCCCCA GCCCCCGCGC CCAGAGAGCA GGAGCCCGGC     420

AGCGGGTGAC GAGGTCGCCG GGACTGGGAG CCGGTGCGGG GGAGGCGGGC CCCGCGGGGC     480

GTGACGCACC GAGCTGGGAG GGCCGGGGCG GGGCAGCCGA GCAGGCTGCA TATAAGGGCG     540

GCGGCCGGGC GCCAAAGCCA GAGCAAGCGG CCTGTGCCCA GATCCTGGGA GAACCCCAGC     600

CGAGCCCAGC CTAGCCCGAG CCCAGCCCGA GCGAAGCCGG AGCCCAAGC CCGAGCCGCG      660

CCCAGCCCGA GCAGAGCCCT CCAGCCGCTC ACCCCGCGTG CCACCCCAGC GACCCTCAGC     720

CGCTCTCTGC CCTTCTCTCG GCCCCGCGCC CGCCCTCGCG GCCCCTCTGC CCAATGAAAC     780

TGGCCGCGAT GATCAAGAAG ATGTGCCCGA GCGACTCGGA GCTGAGTATC CCGGCCAAGA     840
```

-continued

```
ACTGCTATCG CATGGTCATC CTCGGCTCGT CCAAGGTGGG CAAGACGGCC ATCGTGTCGC    900
GCTTCCTCAC CGGCCGCTTC GAGGACGCCT ACACGCCTAC CATCGAGGAC TTCCACCGCA    960
AGTTCTACTC CATCCGCGGC GAGGTCTACC AGCTCGACAT CCTCGACACG TCCGGCAACC   1020
ACCCGTTCCC CGCCATGCGG CGCCTCTCCA TCCTCACAGG TGAGCCGGGG GCCGGGCAGG   1080
TGCGGGAGGG AAGGGCGGGG AACCCTCGGC CAGGGCGCCC CGCGAGCGCC GGTCCGGCTG   1140
CTGCGCGCCG AGTAGTGCGC TTCGCGCTTA GAGAGGCTAG CGCGCCCCGC GCGGCCTCAA   1200
AGTCAGCCCG ACTTGTCCCC TGGGCGGCCA CCCTCACCTT CTCCTTTTCT GCTCTCTGTG   1260
CCCCCTCTAG GAGACGTTTT CATCCTGGTG TTCAGTCTGG ACAACCGCGA CTCCTTCGAG   1320
GAGGTGCAGC GGCTCAGGCA GCAGATCCTC GACACCAAGT CTTGCCTCAA GAACAAAACC   1380
AAGGAGAACG TGGACGTGCC CCTGGTCATC TGCGGCAACA AGGGTGACCG CGACTTCTAC   1440
CGCGAGGTGG ACCAGCGCGA GATCGAGCAG CTGGTGGGCG ACGACCCCA GCGCTGCGCC   1500
TACTTCGAGA TCTCGGCCAA GAAGAACAGC AGCCTGGACC AGATGTTCCG CGCGCTCTTC   1560
GCCATGGCCA AGCTGCCCAG CGAGATGAGC CCAGACCTGC ACCGCAAGGT CTCGGTGCAG   1620
TACTGCGACG TGCTGCACAA GAAGGCGCTG CGGAACAAGA AGCTGCTGCG GGCCGGCAGC   1680
GGCGGCGGCG GCGGCGACCC GGGCGACGCC TTTGGCATCG TGGCACCCTT CGCGCGCCGG   1740
CCCAGCGTAC ACAGCGACCT CATGTACATC CGCGAGAAGG CCAGCGCCGG CAGCCAGGCC   1800
AAGGACAAGG AGCGCTGCGT CATCAGCTAG GAGCCCCGCC GCGCTGGCGA CACAACCTAA   1860
GGAGGACCTT TTTGTTAAGT CAAATCCAAC GGCCCGGTGC GCCCCAGGCC GGGAGCGCGC   1920
GCGGACTGGC GTCTCCCCTC CCGGCGATCC GCCCCCAGCA CTGGGGAGGC GCCACTGAAC   1980
CGAGAAGGGA TGGTCATCTG CTCCGGAAGG AAAGAGAACG GGCCAAGACT GGGACTATTC   2040
CCCACCCCCG GTCCCCCATT GAGGCCCGCC ACCCCCATAA CTTTGGGAGC GAGGGCCCAG   2100
CCGAGGGTGG ATTTATCTTC TCAAAGACCT AAGAGTGAGC GCGGGGTGGG GGAGGGATGT   2160
GAAGTTATCC AGCCTCTGCT AGGCTTCAAG AAACCGTCAT GCCCGCTTGA GGGTCAGGAC   2220
CCACGGGCA TTATCTTGTC TGTGATTCCG GGTTGCTGTG ACAGCCGGTA GAGCCTCTGC   2280
CCTCCCGAAA CTAAGCGGGG GGGCGTGGGT CAAATCATAG CCAAGTGACT TGTTTACATG   2340
TGAGTGAAAC TGCACAAAGG AACACAAAAC AAAACTTGCA CTTTAACGGT AGTTCCGGTG   2400
TCAACATGGA CACGAACAAA ACCTTACCCA GGTGTTTATA CTGTGTGTGT GTGAGGTCTT   2460
TAAAGTTATT GCTTTATTTG GTTTTTTAAT ATACAATAAA ATAATTTAAA ATGGAAAACC   2520
GGTTTTTTTT TTTTTTTTTT TTTTTTTTGC TTTTAGAGAT GGCTGGAGTG GGGAAGGGTG   2580
GGGAGAAGGA AAGGGCTGGG CTTTGACTTA GGTGGAACTA GAACTTACCT TCCCCAGAAC   2640
TGGAAAATAA CCCTGGCCTT CTGAAGGCAG CTTCAGCTGC CAGAAAAGCC CCAGATGCCT   2700
GGGGCATCTA TGTAGGGGAT GGTTCCCTAG AAAACCGGGA AGAATATAAA GGATTTCAGG   2760
GTCTCCCCTG GAGATGAACT CTTTCTAGCC ATCCACCCGC TTAATTTTCT TTGGGTTAGA   2820
TGACAAAAGG CCTCATTTTC TGAGAGAATG TTCTGAATTC TTCAGCGTAA AAGCCACTGG   2880
AACTGTGCCT AACCATTTTG TCACCAGACT CAGTGTGGGC CCAGGCAAAC TTTCGGACTG   2940
TTGGAGGCAT CAGTCAGGCC CTGGGGAAAG AGCCTGAGAC CCCATCTGGA AACAGGACCA   3000
TCCTGGCGCG CCCCCACCAC CCGCTCACTC CAGGGTGCCA CCCTGTCTGG AAACAGCTAA   3060
CTCCTCAGCC TCTGCTCCCC TCTAGCTCCA GGAAGTGCTC CTGGCCAGGT GTAGAGCCCC   3120
ATCCCCCTTC AGCCTTGCTG TCTCGGTCTC ATGGCTAAGG CACCCCAGAA CACCAATCTC   3180
TCTGCCACTA GTACTGCAAA CCTGTTGGTG GGTGACACCT GCCAAGCCTC TAATTCTTCA   3240
```

```
CCCCGGGAAG AGAGAACACC CTCGGCATGG GCTCACTGTG GGGATTAAGT GTGATGTTTG      3300

AAAAGTACTT AGCATAAATG CCGGCCACCC AGTAATCCAA GTAATTGGTG GCTTTCAGAG      3360

GACGCTCAGC CCTGTGAGAG ACACTCAAAA TTGTCCTAGA AGGATTTCAA CCCTGCTCTG      3420

GTGAGGGCGG CTCCCCACAG GACTGAACCT CCTCGAGTCA CCAAAAGGCA CCCCCCACCT      3480

CCCCCCTCCA AAAATAAAAG GCAACTAAGG ACAGCCCAGG GGCCCGTGAC AGGCAGGGGC      3540

AGGGATGACC CGCCAGGCAA ACTGCCCTTG AGGCCAGCCG GGAGAGGAGT TCCTGTTCCA      3600

CACTGGTTCA GCGGGTGTGT GTGCTGGGGC GGGTGTGTGT GCTGGGGCGG AGGGAGTGAG      3660

GAGCAGAGGT GTGGTTGTGT CTGAAGAGAC TGAGAGAAAC ATTTTCCTCT CAACTATCTG      3720

AGAGCCATCC CACTATGAAT TTCTCAGTAC AAAAAGCATT ATGTCCTGAG ACAGCAGAGC      3780

ATAAGTCCTT TTAATTATGT GTTTGAAAAA TGTCACAAGT CAAAAAAGGA ACACAAGGCA      3840

GGCTCCGGCT CCCTCCACCC CCGTGAGGAG CCCTTGTCCA TTTCAGCCTT GCACTCAGAA      3900

AGACCCCGGG GGTCTTGTAG TTCCACGTGC TTCATGTTTC GTGGTATCTG TCAGAGCCTT      3960

AAAACAGGCC CACCCACTAC TGTGAA                                          3986

(2) INFORMATION FOR SEQ ID NO:4:

(i) SEQUENCE CHARACTERISTICS:
        (A) LENGTH: 1689 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 132..971

(xi) SEQUENCE DESCRIPTION: SEQ ID NO:4:

CCCGCTGCCT GTACTCAAGA TTCCAGGCCA GCTCGCGCGG TCCCGAAGCC AAACTCTTCC       60

ACCACTCCGG CGCCCTCTGC AGCCCTCTAC CTTCTCTCAG CCACGCATCT GCCCTGGGGC      120

CCCTCTGCCC A ATG AAA CTG GCC GCG ATG ATC AAG AAG ATG TGC CCA AGC      170
             Met Lys Leu Ala Ala Met Ile Lys Lys Met Cys Pro Ser
              1               5                  10

GAC TCT GAA CTG AGT ATC CCG GCC AAG AAC TGC TAC AGG ATG GTC ATC      218
Asp Ser Glu Leu Ser Ile Pro Ala Lys Asn Cys Tyr Arg Met Val Ile
         15                  20                  25

CTC GGC TCA TCC AAA GTG GGC AAG ACG GCC ATC GTG TCG CGC TTC CTC      266
Leu Gly Ser Ser Lys Val Gly Lys Thr Ala Ile Val Ser Arg Phe Leu
 30                  35                  40                  45

ACG GGC CGC TTC GAG GAC GCT TAC ACC CCT ACC ATT GAA GAC TTC CAC      314
Thr Gly Arg Phe Glu Asp Ala Tyr Thr Pro Thr Ile Glu Asp Phe His
                 50                  55                  60

CGA AAG TTT TAC TCG ATC CGC GGC GAA GTC TAC CAG TTG GAC ATA CTG      362
Arg Lys Phe Tyr Ser Ile Arg Gly Glu Val Tyr Gln Leu Asp Ile Leu
             65                  70                  75

GAC ACA TCT GGC AAT CAT CCG TTT CCC GCC ATG CGG CGC CTC TCT ATC      410
Asp Thr Ser Gly Asn His Pro Phe Pro Ala Met Arg Arg Leu Ser Ile
         80                  85                  90

CTC ACA GGA GAC GTT TTC ATT CTG GTG TTC AGC TTA GAC AAC CGC GAC      458
Leu Thr Gly Asp Val Phe Ile Leu Val Phe Ser Leu Asp Asn Arg Asp
 95                  100                 105

TCC TTC GAG GAG GTG CAA AGG CTC AAA CAG CAG ATC CTA GAC ACC AAG      506
Ser Phe Glu Glu Val Gln Arg Leu Lys Gln Gln Ile Leu Asp Thr Lys
110                 115                 120                 125
```

-continued

```
TCC TGT CTC AAG AAC AAA ACC AAA GAG AAT GTG GAC GTG CCG CTG GTC    554
Ser Cys Leu Lys Asn Lys Thr Lys Glu Asn Val Asp Val Pro Leu Val
            130             135             140

ATT TGC GGT AAC AAA GGG GAC CGG GAC TTC TAC CGC GAA GTG GAG CAG    602
Ile Cys Gly Asn Lys Gly Asp Arg Asp Phe Tyr Arg Glu Val Glu Gln
            145             150             155

CGG GAG ATT GAG CAG CTG GTG GGC GAT GAC CCT CAG CGT TGT GCC TAC    650
Arg Glu Ile Glu Gln Leu Val Gly Asp Asp Pro Gln Arg Cys Ala Tyr
            160             165             170

TTC GAG ATC TCG GCC AAG AAG AAT AGC AGC CTG GAC CAG ATG TTC CGT    698
Phe Glu Ile Ser Ala Lys Lys Asn Ser Ser Leu Asp Gln Met Phe Arg
        175             180             185

GCG CTC TTT GCC ATG GCC AAG CTG CCT AGC GAG ATG AGC CCT GAC TTG    746
Ala Leu Phe Ala Met Ala Lys Leu Pro Ser Glu Met Ser Pro Asp Leu
190             195             200             205

CAC CGC AAG GTG TCT GTG CAG TAC TGT GAC GTG CTG CAC AAA AAG GCT    794
His Arg Lys Val Ser Val Gln Tyr Cys Asp Val Leu His Lys Lys Ala
            210             215             220

CTG AGG AAC AAG AAG CTT CTG CGT GCG GGC AGC GGA GGT GGG GGC GAC    842
Leu Arg Asn Lys Lys Leu Leu Arg Ala Gly Ser Gly Gly Gly Gly Asp
            225             230             235

CAC GGA GAT GCC TTT GGC ATC TTG GCG CCC TTT GCT CGC AGA CCT AGC    890
His Gly Asp Ala Phe Gly Ile Leu Ala Pro Phe Ala Arg Arg Pro Ser
            240             245             250

GTG CAT AGC GAC CTC ATG TAC ATT CGT GAG AAA ACC AGT GTC AGC AGC    938
Val His Ser Asp Leu Met Tyr Ile Arg Glu Lys Thr Ser Val Ser Ser
            255             260             265

CAG GCT AAG GAC AAG GAG CGC TGT GTC ATC AGT TAGGAGCCCC CAGGGTCAGT    991
Gln Ala Lys Asp Lys Glu Arg Cys Val Ile Ser
270             275             280

CAGCCACACA ACCTGAGGAC CTTTTTTGTT CAAAAGTCAA ATCGGTTTCC CAGGCTAACC   1051

TGTGCACTCC GTGCCCCAAG AGCGCCAGCT GGCCTCCTCC CTCCCTCCCT GAGACCCAGC   1111

CCTGTGCACC AGGGAGATGC TGCCAAGACA GTAAGGGACA GTCATCTGCT GTGAGAGGAA   1171

AGAACTAGCT AAGACTGGGA CTTTCGCCTC CGATTCTGGG ATGCCAGGAC CCAGCAGAGG   1231

GTTAGTTGGC GTTTTTCTCA GAGACTTTGA GAGTGTGTGA AGGGCTTCGG CCTCTGAGAC   1291

TTCAAGTAAC TGTGCGGCTT GCTGTGGGGC CAGGACTAAC AGGGCATTAT CTCGTCTGTG   1351

ATTGGTGTTG CCATGACCGC TGTCAGCCAC CTCTGTCCTC AGCAAACTGG AAACTTTGGC   1411

TCGAGGTGGG GGTTCAATCA TAGCCAGACA ACTTGTTTAC ATGTGTGTGT GTGTGTAATT   1471

ACCCAAAAGG AAAACAAAAC ACAAAACTTG CACTTTAACA GTTCCAGTGT CAACGTGACA   1531

TGAACAAAAT CTCTACATTT CTATTGTGTG AGGTCTTTAT TATTTTTTTT AATTTAAAAT   1591

AAAATAATTT TAAAATGGAA AAAAAAAAA AAAAAAAAA AAGGGCGGCC GCTCTAGAGG    1651

ATCCAAGCTT ACGTACGCGT GCATGCGACG TCATACTC                          1689
```

(2) INFORMATION FOR SEQ ID NO:5:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO:5:

```
Met Lys Leu Ala Ala Met Ile Lys Lys Met Cys Pro Ser Asp Ser Glu
 1               5                  10                  15
```

-continued

```
Leu Ser Ile Pro Ala Lys Asn Cys Tyr Arg Met Val Ile Leu Gly Ser
            20                  25                  30
Ser Lys Val Gly Lys Thr Ala Ile Val Ser Arg Phe Leu Thr Gly Arg
        35                  40                  45
Phe Glu Asp Ala Tyr Thr Pro Thr Ile Glu Asp Phe His Arg Lys Phe
    50                  55                  60
Tyr Ser Ile Arg Gly Glu Val Tyr Gln Leu Asp Ile Leu Asp Thr Ser
 65                 70                  75                  80
Gly Asn His Pro Phe Pro Ala Met Arg Arg Leu Ser Ile Leu Thr Gly
                85                  90                  95
Asp Val Phe Ile Leu Val Phe Ser Leu Asp Asn Arg Asp Ser Phe Glu
            100                 105                 110
Glu Val Gln Arg Leu Lys Gln Gln Ile Leu Asp Thr Lys Ser Cys Leu
        115                 120                 125
Lys Asn Lys Thr Lys Glu Asn Val Asp Val Pro Leu Val Ile Cys Gly
    130                 135                 140
Asn Lys Gly Asp Arg Asp Phe Tyr Arg Glu Val Glu Gln Arg Glu Ile
145                 150                 155                 160
Glu Gln Leu Val Gly Asp Asp Pro Gln Arg Cys Ala Tyr Phe Glu Ile
                165                 170                 175
Ser Ala Lys Lys Asn Ser Ser Leu Asp Gln Met Phe Arg Ala Leu Phe
            180                 185                 190
Ala Met Ala Lys Leu Pro Ser Glu Met Ser Pro Asp Leu His Arg Lys
        195                 200                 205
Val Ser Val Gln Tyr Cys Asp Val Leu His Lys Lys Ala Leu Arg Asn
    210                 215                 220
Lys Lys Leu Leu Arg Ala Gly Ser Gly Gly Gly Asp His Gly Asp
225                 230                 235                 240
Ala Phe Gly Ile Leu Ala Pro Phe Ala Arg Arg Pro Ser Val His Ser
                245                 250                 255
Asp Leu Met Tyr Ile Arg Glu Lys Thr Ser Val Ser Ser Gln Ala Lys
            260                 265                 270
Asp Lys Glu Arg Cys Val Ile Ser
        275                 280
```

(2) INFORMATION FOR SEQ ID NO:6:

(i) SEQUENCE CHARACTERISTICS:
        (A) LENGTH: 3079 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CCAGCGCACG TAGGTCTGGA GCACAGCCTC AGGCTCCAAG GCGGAGGTCA CTGCGTCTAG      60

GAGGAGCCCG GAGCGTCCGG GGGCGGGACG TGACGCACCT TGGCTGGGAG GTGCCAGCCC     120

AGGCTTCGGT CAGCTGCATA TAAGAGTGGT GTGAGGCGCG GAAAGCCTGA GCCCGCTGCC     180

TGTACTCAAG ATTCCAGGCC AGCTCGCGCG GTCCCGAAGC CAAACTCTTC CACCACTCCG     240

GCGCCCTCTG CAGCCCTCTA CCTTCTCTCA GCCACGCATC TGCCCTGGGG CCCCTCTGCC     300

CAATGAAACT GGCCGCGATG ATCAAGAAGA TGTGCCCAAG CGACTCTGAA CTGAGTATCC     360

CGGCCAAGAA CTGCTACAGG ATGGTCATCC TCGGCTCATC CAAAGTGGGC AAGACGGCCA     420
```

```
TCGTGTCGCG CTTCCTCACG GGCCGCTTCG AGGACGCTTA CACCCCTACC ATTGAAGACT    480

TCCACCGAAA GTTTTACTCG ATCCGCGGCG AAGTCTACCA GTTGGACATA CTGGACACAT    540

CTGGCAATCA TCCGTTTCCC GCCATGCGGC GCCTCTCTAT CCTCACAGGT GAGTGGGGGA    600

CCGACAGGGA CCGTGGGGAG GGAATCTGCG GGGAGCGGAT GGGGCGGTGT GTTGTGCTTG    660

GGGCTGTGCT GTCTGCTGCT CCGTGCTTGG CAGCTGCCCT CACCTTTCCA CTCGTTCCCT    720

TGTAGGAGAC GTTTTCATTC TGGTGTTCAG CTTAGACAAC CGCGACTCCT TCGAGGAGGT    780

GCAAAGGCTC AAACAGCAGA TCCTAGACAC CAAGTCCTGT CTCAAGAACA AAACCAAAGA    840

GAATGTGGAC GTGCCGCTGG TCATTTGCGG TAACAAAGGG GACCGGGACT TCTACCGCGA    900

AGTGGAGCAG CGGGAGATTG AGCAGCTGGT GGGCGATGAC CCTCAGCGTT GTGCCTACTT    960

CGAGATCTCG GCCAAGAAGA ATAGCAGCCT GGACCAGATG TTCCGTGCGC TCTTTGCCAT   1020

GGCCAAGCTG CCTAGCGAGA TGAGCCCTGA CTTGCACCGC AAGGTGTCTG TGCAGTACTG   1080

TGACGTGCTG CACAAAAAGG CTCTGAGGAA CAAGAAGCTT CTGCGTGCGG GCAGCGGAGG   1140

TGGGGGCGAC CACGGAGATG CCTTTGGCAT CTTGGCGCCC TTTGCTCGCA GACCTAGCGT   1200

GCATAGCGAC CTCATGTACA TTCGTGAGAA AACCAGTGTC AGCAGCCAGG CTAAGGACAA   1260

GGAGCGCTGT GTCATCAGTT AGGAGCCCCC AGGGTCAGTC AGCCACACAA CCTGAGGACC   1320

TTTTTTGTTC AAAAGTCAAA TCGGTTTCCC AGGCTAACCT GTGCACTCCG TGCCCCAAGA   1380

GCGCCAGCTG GCCTCCTCCC TCCCTCCCTG AGACCCAGCC CTGTGCACCA GGGAGATGCT   1440

GCCAAGACAG TAAGGGACAG TCATCTGCTG TGAGAGGAAA GAACTAGCTA AGACTGGGAC   1500

TTTCGCCTCC GATTCTGGGA TGCCAGGACC CAGCAGAGGG TTAGTTGGCG TTTTTCTCAG   1560

AGACTTTGAG AGTGTGTGAA GGGCTTCGGC CTCTGAGACT TCAAGTAACT GTGCGGCTTG   1620

CTGTGGGGCC AGGACTAACA GGGCATTATC TCGTCTGTGA TTGGTGTTGC CATGACTGCT   1680

GTCAGCCACC TCTGTCCTCA GCAAACTGGA AACTTTGGCT CGAGGTGGGG GTTCAATCAT   1740

AGCCAGACAA CTTGTTTACA TGTGTGTGTG TGTGTAATTA CCCAAAAGGA AAACAAAACA   1800

CAAAACTTGC ACTTTAATAG TTCCAGTGTC AACGTGACAT GAACAAAATC TCTACATTTC   1860

TATTGTGTGA GGTCTTTATT ATTTTTTTTA ATTTAAAATA AAATAATTTT AAAATGGAAA   1920

ATGGTGCTTC GCTTTGCTTT TGCTTTTAGG CTTCCTGCCT CGGTGGCAGT GGCCAAGAAC   1980

TGGAAAAGGA CCTGGCTTTC AGAATATGGT CTCCCACTTC CAAGTGGGAC CTTCTGGCTT   2040

TCTGTCTACA CTCTGCCCGG CCTGGCCTGT AACAGAGGGC CTTGTTTTAG AGAATATTCA   2100

TACTCTCCTC CACACAGCCC ATCTGTTACT CATCATAGAA GGCAACAGAA AGCTGCCACA   2160

CTTGAAACGC TAACCTTGAT TACCACAAAC ATGGAGGCTG AGGTGGAGAG GTGTGGCAGG   2220

GAAGAGGCCT GCACTTAACG TTCATTCCTT GCCCCAGGGC TGCCGCAGGA CCTGGACAGG   2280

GAAAGTACAG ATGGGTGGAG TGCAGCTCCC AGAAGCTCTC GAGCAGGTGG GGCCCACCTC   2340

CTCTGCACCT TCCTAACTCC CTGTGGCTAA GGGCTCATAG TTTGTGACCC AGATCTCCTT   2400

GCCACTCCTA CGGTCAACTT AGGGCAAGTG TCGCCTTCCA AGTCTCCAAT CTGCAGCTG    2460

AGAAATCGAG GCACTCTGTG CAGGGGTCAA CATGGTCTCC AAGGAGTCAG CACAACTGCT   2520

GCAGCCGCCC AGCCAAATAC TTGGTTTTTC CAGGGTCTTG ACCTTCGGGG ATGCTCAAAA   2580

TTGTCTTGGG ACCGGGGGAG GAAGGGTCTT GTCAACCCTG CTTTGGGAAG GCCACTTGC    2640

AGGGAACTGT ACCTCCTCAA ATCTCAGAAA GGCACTCACT TCTCAACAAT GAATGGCTGG   2700

GCTCCCCAGG GTCCCCTGCA GGAGACGTGT AGGCTTTGTG CTCATTTAAC AGATGTACAT   2760

GCTGGGCGGA AGGAGGAGCG CAGTGAACAT TTTTGCCTCT ACACCACCCA CTCAACACAC   2820
```

-continued

```
CACTCTAATT CTTCATTTTA AAGACCTGCA ATCCCAGGGT CTGACTGCTA GCCCTGAGAG    2880

AGACAGAGAC AACAGGCAAA CCATGTGTCC TGAGAACAGA ACATACTTTT AATTACATAT    2940

GTGAAAACAT GACAGGTCAA CACACTGGAA CAGAGAAGCC TCCGAGCCTC CAGCCCTTCG    3000

AGGAAGCCTT CTTTCTTCCC TGTCAGGAAG ATCCGAAGCT CCTGCATTTC ACGTGCTCTG    3060

CCCTTACAGG AACTGGGCA                                                  3079
```

(2) INFORMATION FOR SEQ ID NO:7:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Thr Gly Arg Gly Arg Pro Arg Gly Gly Pro Gly Pro Gly Asp Pro
 1               5                  10                  15

Pro Pro Ser Glu Thr His Lys Leu Val Val Gly Gly Gly Gly Val
                20                  25                  30

Gly Lys Ser Ala Leu Thr Ile Gln Phe Ile Gln Ser Tyr Phe Val Ser
        35                  40                  45

Asp Tyr Asp Pro Thr Ile Glu Asp Ser Tyr Thr Lys Ile Cys Ser Val
50                  55                  60

Asp Gly Ile Pro Ala Arg Leu Asp Ile Leu Asp Thr Ala Gly Gln Glu
65                  70                  75                  80

Glu Phe Gly Ala Met Arg Glu Gln Tyr Met Arg Ala Gly His Gly Phe
                85                  90                  95

Leu Leu Val Phe Ala Ile Asn Asp Arg Gln Ser Phe Asn Glu Val Gly
                100                 105                 110

Lys Leu Phe Thr Gln Ile Leu Arg Val Lys Asp Arg Asp Asp Phe Pro
            115                 120                 125

Val Val Leu Val Gly Asn Lys Ala Asp Leu Glu Ser Gln Arg Gln Val
    130                 135                 140

Pro Arg Ser Glu Ala Ser Ala Phe Gly Ala Ser His His Val Ala Tyr
145                 150                 155                 160

Phe Glu Ala Ser Ala Lys Leu Arg Leu Asn Val Asp Glu Ala Phe Glu
                165                 170                 175

Gln Leu Val Arg Ala Val Arg Lys Tyr Gln Glu Gln Glu Leu Pro Pro
            180                 185                 190

Ser Pro Pro Ser Ala Pro Arg Lys Lys Gly Gly Gly Cys Pro Cys Val
    195                 200                 205

Leu Leu
    210
```

(2) INFORMATION FOR SEQ ID NO:8:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CCTGCTCTGA CCCCGGGTGG CCCCTACCCC TGGCGACCCC TCACGCACAC AGC          53
```

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CGCTCACCCC GGGTGCCACC CCCTGGCGGC CCCTC                              35
```

MAMMALIAN BLOOD LOSS-INDUCED GENE, KD312

BACKGROUND

1. Field of the Invention

This invention relates to a novel polypeptide designated kd312 and related polypeptides that have an effect on apoptosis, to novel nucleic acid molecules encoding such polypeptides, and to other related aspects.

2. Description of Related Art

Apoptosis

Normal development and tissue homeostasis in animals require the total cell numbers to be kept in an appropriate range. This is achieved by several highly regulated processes involving cell proliferation, survival, and elimination through programmed cell death (apoptosis). An imbalance between the rates of cell production and cell loss can result in serious human diseases such as cancer, disorders of the immune system, and neurodegenerations (reviewed by Rudin, C. M., and Thompson, C. B., Ann. Rev. Med. 48: 267–81 (1997)).

Apoptosis appears to be an evolutionarily conserved, highly organized program of active cell destruction (reviewed by Miura, M., and Yuan, J., Curr. Topics. Dev. Biol. 32: 139–174 (1996); Vaux, D. L. and Strasser, A., Proc. Natl. Acad. Sci. USA 93: 2239–2244 (1996)). In the nematode *Caenorhabditis elegans,* 14 genes involved in apoptosis have been identified. Among these, the ced-3 gene encodes a cysteine protease of the capsase family and is a key effector in the cell death pathway. The gene product of ced-4 appears to be an adaptor protein which activates ced-3 upon receiving apoptosis signals (Vaux, D. L., Cell 90: 389–390 (1997). The ced-9 gene, a potent suppresser of programmed cell death, negatively regulates the activity of ced-3, probably through ced-4. In mammalian cells, multiple capsases have been identified and shown to be part of the cell death machinery (Henkart, P. A., Immunity 4: 195–201 (1996)). The bcl-2 proto-oncogene appears to be the prototype of mammalian homologs of ced-9 (Vaux, D. L., Cory, S., and Adams, J. M., Nature 335: 440–442 (1988); Vaux, D. L., Weissman, I. L., and Kim, S. K., Science 258: 1955–1957 (1992); Hengartner, M. O., and Horvitz, H. R., Cell 76: 665–676(1994)).

Other members of the bcl-2 family consist of those (such as bcl-XL) that are functionally similar to bcl-2 which can block apoptosis; and others (bax, for example) that have the opposite activity (Boise, L. H., Gonzalez-Garcia, M., Postema, C. E., Ding, L., Lindsten, T., Turka, L. A., Mao, X., Nunez, G., and Thompson, C. B., Cell 74: 597–608 (1993); Oltvai, Z. N., Milliman, C. L., and Korsmeyer, S. J., Cell 74: 609–619 (1993)). Although the molecular mechanism is still unclear, recent evidence showed that bcl-2 can block the release of cytochrome c from mitochondria (Kluck, R. M., Bossy-Weitzel, E., Green, D. R., and Newmeyer, D. D., Science 275: 1132–1136 (1997)). In addition, bcl-2 appears to directly inhibit capsase activation by binding to the mammalian ced-4 homolog (Zou, H., Henzel, W. J., Liu, X., Lutzchg, A., and Wang, X., Cell 90: 405–413 (1997)). Other genes besides the bcl-2 family have also been implicated in programmed cell death as well. For example, the transcription factors c-myc and NF-κB may be involved in transducing signals for cell death or survival (Askew, D. S., Ashmun, R. A., Simmons, B. C., and Cleveland, J. L., Oncogene 6: 1915–1922 (1991); Evan, G. I., Wyllie, A. H., Gilbert, C. S., Littlewood, T. D., Land, H., Brooks, M., Waters, C. M., Penn, L. Z., and Hancock, D. C., Cell 69: 119–128 (1992); Hsu, H., Xiong, J., and Goeddel, D. V., Cell 81: 495–504 (1995); Beg, A. A., and Baldwin, A. S., Science 274: 782–784 (1996); Wang, C-Y., Mayo, M. W., and Baldwin, A. S., Science 274: 784–787 (1996)). The tumor suppresser gene p53, which is mutated in over 50% of human cancers, plays an essential role in radiation induced apoptosis in a wide variety of cell types (reviewed by Carson, D. A., Lancet 346: 1009–1011 (1995)).

Blood Loss and Apoptosis

Massive blood loss may deprive animal organs of most of their oxygen supply and lead to cell damage and both necrotic cell death and apoptosis. It is known that many proteins are synthesized in response to low oxygen tensions (hypoxia). Among these proteins, a few with known functions such as erythropoietin (for stimulating erythroid progenitors), vascular endothelial growth factor (for angiogenesis), or the HAP1 protein (for DNA repair), are all known to assist in cell survival during times of hypoxia. Some of the hypoxia-induced proteins may play important roles in cell survival also through reduction or inhibition of apoptosis. In view of recent evidence indicating that alterations in the apoptosis threshold contribute to the pathological cell death or growth in a number of human diseases such as neurodegenerative disorders, ischemic injury, AIDS, and cancers (Thompson, C. B., Science, 267: 1456–1462 (1995)), it is important to identify key factors that protect cells from apoptotic death.

Although a number of cell death related genes and proteins are now known, there remains a need to identify additional such genes and proteins and to determine their biological activity.

Accordingly, it is an object of the present invention to provide novel compounds that are associated with cell death, especially when caused by hypoxia, in mammals.

It is a further object of the invention to provide a method of treating diseases associated with cell death such as those set forth herein.

These and other objects will be apparent to one of ordinary skill in the art from the present disclosure.

SUMMARY OF THE INVENTION

To understand better the molecular events governing apoptosis, screening for genes whose expression level is significantly altered during hypoxia induced by blood loss was carried out.

A gene, kd312, has been isolated from rat kidneys and identified to be a gene highly induced after severe blood loss. This gene was also found to be induced in the liver and thymus of the same animal. It was present in the brain but not detected in the bone marrow, heart, or spleen of this animal. The levels of induction in the kidneys can be correlated to the severity of blood loss. The human homolog of this gene was also isolated. The kd312 protein is well conserved between rats and humans. The deduced amino acid sequence of the rat kd312 protein (280 amino acids) shares 97.5% identity with that of the human counterpart (281 amino acids). The kd312 protein is distantly related to the Ras protein family and the human kd312 is most homologous (33.8%) with the R-Ras member of the human Ras family. Similar to Ras proteins, kd312 carries a C-terminal CAAX motif and a GTP-binding site close to the amino terminus. Unlike the Ras genes, neither the rat nor the human kd312 gene induces focus development following expression in NIH3T3 cells. Expression of kd312 in human embryonal kidney cell line 293 protects the cells from apoptosis similar to the effect observed with expression of the bcl-2 gene in this cell line.

The present invention embodies various aspects, as set forth in the following:

In a first embodiment, the present invention provides a nucleic acid molecule encoding a polypeptide selected from the group consisting of:

(a) the nucleic acid molecule of SEQ ID NO:1 or SEQ ID NO:3;

(b) a nucleic acid molecule encoding the polypeptide of SEQ ID NO:2 or a biologically active fragment thereof;

(c) a nucleic acid molecule that encodes a polypeptide that is at least 85 percent identical to the polypeptide of SEQ ID NO:2;

(d) a nucleic acid molecule that hybridizes under stringent conditions to any of (a)–(c) above; and (e) a nucleic acid molecule that is the complement of any of (a)–(d) above.

In another embodiment, the present invention provides a nucleic acid molecule encoding a polypeptide selected from the group consisting of (a') the nucleic acid molecule of SEQ ID NO:4 or SEQ ID NO:6;

(b') a nucleic acid molecule encoding the polypeptide of SEQ ID NO:5 or a biologically active fragment thereof;

(c') a nucleic acid molecule that encodes a polypeptide that is at least 85 percent identical to the polypeptide of SEQ ID NO:5;

(d') a nucleic acid molecule that hybridizes under stringent conditions to any of (a')–(c') above; and (e') a nucleic acid molecule that is the complement of any of (a')–(d') above.

In another embodiment, the invention provides vectors comprising these nucleic acid molecules, and host cells, either prokaryotic or eukaryotic, comprising the vectors.

The invention further provides a kd312 polypeptide selected from the group consisting of:

(a) the polypeptide of SEQ ID NO:2;

(b) a polypeptide that is at least 85 percent identical to the polypeptide of (a); and (c) a biologically active fragment of any of (a)–(b).

The invention further provides a kd312 polypeptide selected from the group consisting of:

(a') the polypeptide of SEQ ID NO:5;

(b') a polypeptide that is at least 85 percent identical to the polypeptide of (a'); and (c') a biologically active fragment of any of (a')–(b').

In another embodiment, the invention provides a process for producing a kd312 polypeptide, wherein the polypeptide may be SEQ ID NO:2 or SEQ ID NO:4 or a biologically active fragment thereof, and wherein the process comprises:

(a) expressing a polypeptide encoded by a kd312 nucleic acid molecule in a suitable host; and (b) isolating the polypeptide.

The invention further provides anti-kd312 antibodies.

The above and additional related aspects of the invention will be better appreciated by referring to the figures which are described in the following section.

BRIEF DESCRIPTION OF THE DRAWINGS

FIG. 2 shows a comparison of the human and rat kd312 protein sequences (SEQ ID NOS:2 and 5, respectively). The GTP-binding site close to the N-terminus and the C-terminal CAAX motif are underlined.

FIG. 3 shows a comparison of the human kd312 and R-Ras proteins (SEQ ID NOS:2 and 7, respectively). Only regions of both proteins sharing homology are shown.

FIG. 5 shows the genomic sequence and structure of human kd312 (SEQ ID NO:3) The two coding regions (exons) and the amino acid residues they encode are shown. The GC-rich stretch recognized by the transcription factor SP1 and the TATA box, both upstream of the coding region and the downstream sequence coding for the polyadenylation signal are underlined. Arrows mark the 5'- and 3'-end of kd312 cDNA and dashed lines mark two segments homologous to two adjacent sequences essential for hypoxia-induction within the promoter region of the Epo gene (FIG. 6).

FIG. 6 shows homologous sequences with the Epo promoter (SEQ ID NO:8) and the human kd312 upstream region (SEQ ID NO:9). P-Epo indicates a minimal sequence segment within the Epo promoter region that is essential for a portion of hypoxia-induction of Epo. The two short sequences homologous to steroid/thyroid hormone receptor response element half-sites within this segment are overlined. Immediately upstream of the kd312 coding region is a region designated 5'-kd312, which contains two sequences highly homologous to the P-Epo sequence as shown. Numbers indicate base positions relative to the Epo transcription start site and the approximate kd312 transcription start site (FIG. 5) respectively, both of wich are defined as +1.

FIG. 7 shows the genomic sequence and structure of rat kd312 (SEQ ID NO:6) The two coding regions (exons) and the amino acid residues they encode are shown. The TATA box, upstream of the coding region and the downstream sequence coding for the polyadenylation signal are underlined. Arrows mark the 5'- and 3'-end of kd312 cDNA.

FIG. 8 shows the cDNA sequence and structure of human kd312 (SEQ ID NO:1).

FIG. 9 shows the cDNA sequence and structure of rat kd312 (SEQ ID NO:4).

FIG. 10 shows Western analysis of human kd312 protein. Human embryonic 293 cells transfected with the vector pCEP4 or pCEP4 carrying human kd312 cDNA were grown and processed for Western blotting with rat anti-kd312 antiserum as described in the Examples section. Lane 1, Benchmark prestained protein ladder (GibcoBRL). Lane 2, 293 cells transfected with pCEP4. Lane 3, 293 cells transfected with pCEP4 carrying human kd312 cDNA insert. Lane 4, human kd312 and *E. coli* thioredoxin fusion protein partially purified from *E. coli* cells carrying human kd312 insert in the expression vector pET-32a(+) (Materials and Methods). In lanes 2 and 3, 150–200 μg proteins, and in lane 4, 5 ng protein were loaded on the gel. The anticipated molecular weight for human kd312 protein is ~32,000 and that for kd312-thioredoxin fusion protein from pET-32a(+) is ~51,000.

DETAILED DESCRIPTION OF THE INVENTION

Figure 1A:
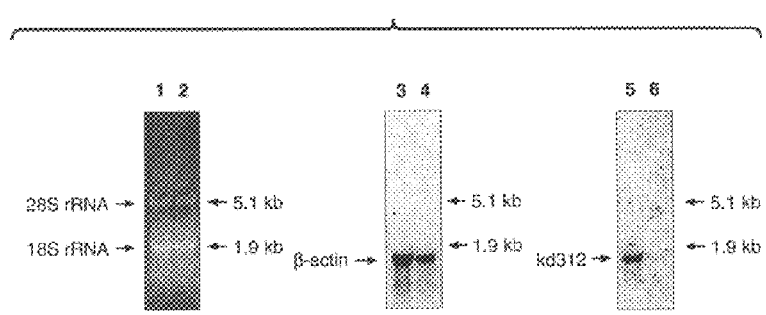
FIGS. 1(A) and (B) depict Northern-blot and RT-PCR analysis of rat total RNA for blood loss-induction of kd312 and Epo genes. (A) Northern-blot of total RNA from a normal animal (lanes 2,4,6) and an animal whose hematocrit reading was 39% of normal level after bleeding (lanes 1,3,5). Lanes 1 and 2, RNA (6 µg) profile in 1% denatured agarose gel. Lanes 3 and 4, same RNA as in lanes 1 and 2 hybridized with a 500 base-pair mouse β-actin gene fragment. Lanes 5 and 6, same RNA as in lanes 3 and 4 hybridized with a 391 base-pair rat kd312 cDNA fragment corresponding to a 3'-untranslated region. The amount of RNA loaded in lane 1 differed slightly from that loaded in lane 2 as indicated by the amounts of rRNAs and β-actin detected in each lane. (B) RT-PCR analysis of the same RNA preparation as in (A) for the presence of Epo message. PCR was carried out following cDNA synthesis from RNA of a normal animal (lanes 2 and 4) and of an animal suffering blood loss (lanes 1 and 3). Lanes 1 and 2, PCR (30 cycles) synthesis of a 190 base-pair rat Epo gene fragment. Lanes 3 and 4, PCR (30 cycles) synthesis of a 267 base-pair rat β-tubulin gene fragment. Lane 5, molecular weight marker. The amounts of RNA used in the two cDNA synthesis reactions differed slightly as indicated by the amounts of β-tubulin gene fragment synthesized by PCR.

Included in the scope of this invention are kd312 polypeptides such as the polypeptides of SEQ ID NO:2 (human kd312-1) or SEQ ID NO: 5 (rat kd312-1), and related biologically active polypeptide fragments and derivatives thereof. Further included within the scope of the present invention are nucleic acid molecules that encode these polypeptides, methods for preparing the polypeptides, and other related aspects.

I. kd312-1 Proteins/Polypeptides, Fragments and Derivatives Thereof

The term "kd312 protein" or "kd312 polypeptide" as used herein refers to any protein or polypeptide having the properties described herein for kd312. The kd312 polypeptide may or may not have an amino terminal methionine, depending, for example, on the manner in which it is prepared. By way of illustration, kd312 protein or kd312 polypeptide refers to:

(1) an amino acid sequence encoded by kd312 nucleic acid molecules as defined in any of the following items:
   (a) the nucleic acid molecules of SEQ ID NOS:1, 3, 4, or 6;
   (b) nucleic acid molecules encoding the polypeptides of SEQ ID NOS:2 or 5, or biologically active fragments thereof;
   (c) nucleic acid molecules encoding polypeptides that are at least 85 percent identical to the polypeptides of SEQ ID NOS:2 or 5;
   (d) nucleic acid molecules that hybridize under stringent conditions to any of (a)–(c) above; and
   (e) nucleic acid molecules that are the complement of any of (a)–(d) above.

(2) naturally occurring allelic variants of the kd312 gene (e.g., the human and rat kd312-1 genes; SEQ ID NOS: 1 and 4, respectively) which result in one or more amino acid substitutions, deletions, and/or insertions as compared to the kd312-1 polypeptides of SEQ ID NO:2 or SEQ ID NO: 5, and/or (3) chemically modified derivatives as well as nucleic acid and or amino acid sequence variants thereof as provided for herein.

The kd312 polypeptides that have use in practicing the present invention may be naturally occurring full length polypeptides, or truncated polypeptides or peptides (i.e, "fragments").

The polypeptides may begin at any one of the three Met residues at positions 1, 6 and 10 of SEQ ID NOS:2 and 5. Depending upon which of these is determined to be the first amino acid of the protein, the sequence may be conveniently numbered by assigning the number 1 to the first Met residue thereof.

The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring kd312 polypeptides (i.e., may contain one or more amino acid deletions, insertions, and/or substitutions as compared with naturally occurring kd312, e.g., kd312-1).

As used herein, the term "kd312 fragment" refers to a peptide or polypeptide that is less than the full length amino acid sequence of naturally occurring kd312 protein but has qualitatively a substantially similar type of biological activity as kd312 polypeptide or kd312 protein described above. Such a fragment may be truncated at the amino terminus, the carboxy terminus, or both, and may be chemically modified. Such kd312 fragments may be prepared with or without an amino terminal methionine. The activity of the fragments may be greater than, the same as, or less than the full-length (mature) kd312 polypeptide. Preferably, the activity of the fragment is ≧50%, more preferably ≧65%, most preferably ≧80%, of the activity of the full-length polypeptide, as measured by a standard activity assay, such as those set forth in the Examples section herein. Some exemplary fragments of this invention include the polypeptides wherein from 1 to 20 amino acids are removed from either the C-terminus, the N-terminus, or both termini, of the kd312 polypeptide.

As used herein, the term "kd312 derivative" or "kd312 variant" refers to a kd312 polypeptide, protein, or fragment that 1) has been chemically modified, as for example, by addition of one or more polyethylene glycol molecules, sugars, phosphates, or other such molecules not naturally attached to wild-type kd312 polypeptide, and/or 2) contains one or more nucleic acid or amino acid sequence substitutions, deletions, and/or insertions as compared to the kd312 amino acid sequence, such as those set forth in FIG. 2.

As used herein, the terms "biologically active polypeptide" and "biologically active fragment" refer to a peptide or polypeptide in accordance with the above description for kd312 wherein the kd312 acts as a kinase that is capable of prolonging survival of cells (e.g., neural or immunological cells) Fragments and/or derivatives of kd312 that are not themselves active in activity assays may be useful as modulators (e.g., inhibitors or stimulants) of the kd312 receptors in vitro or in vivo, or to prepare antibodies to kd312 polypeptides.

The amino acid variants of kd312 of this invention preferably are at least 85% identical to either SEQ ID NO: 2 or SEQ ID NO: 5, more preferably at least about 90% identical, even more preferably at least about 95% identical.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a predetermined portion of one or both sequences). Each computer program provides a "default" opening penalty and a "default" gap penalty, and a scoring matrix such as PAM 250. A standard scoring matrix (see Dayhoff et al., in: *Atlas of Protein Sequence and Structure*, vol. 5, supp.3 [1978]) can be used in conjunction with the computer program. The percent identity can then be calculated using an algorithm contained in a program such as FASTA as:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 85 percent identical will typically have one or more amino acid substitutions, deletions, and/or insertions as compared with wild type kd312. Usually, the substitutions will be conservative so as to have little or no effect on the overall net charge, polarity, or hydrophobicity of the protein but optionally may increase the activity of kd312. Conservative substitutions are set forth in Table I below.

TABLE I

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The invention also encompasses species homologs of kd312; for example, kd312 homologs from a mammalian species such as dog, cat, mouse, rat, monkey, horse, pig, goat, rabbit, sheep and the like are contemplated in addition to human. The sequence of the exemplary rat protein, kd312-1, is provided as SEQ ID NO: 5.

The invention further encompasses chimeric polypeptides, i.e., kd312 attached to all or a portion of another polypeptide. Preferably the chimeric polypeptide comprises kd312 attached to all or a portion of another factor. The polypeptides may be attached N to C terminus, C to C terminus, or N to N terminus. They may be attached directly, or they may be connected via a linker, such as a polyamino acid linker (e.g., poly-Gly).

II. Nucleic Acids

As used herein, the term "kd312" when used to describe a nucleic acid molecule refers to a nucleic acid molecule or fragment thereof, as set forth above.

The term "stringent conditions" refers to hybridization and washing under conditions that permit only binding of a nucleic acid molecule such as an oligonucleotide or cDNA molecule probe to highly homologous sequences. One stringent wash solution is 0.015 M NaCl, 0.005 M NaCitrate, and 0.1 percent SDS used at a temperature of 55–65° C. Another stringent wash solution is 0.2×SSC and 0.1 percent SDS used at a temperature of between 50–65° C. Where oligonucleotide probes are used to screen cDNA or genomic libraries, the following stringent washing conditions may be used. One protocol uses 6×SSC with 0.05 percent sodium pyrophosphate at a temperature of 35–62° C., depending on the length of the oligonucleotide probe. For example, 14 base pair probes are washed at 35–40° C., 17 base pair probes are washed at 45–50° C., 20 base pair probes are washed at 52–57° C., and 23 base pair probes are washed at 57–63° C. The temperature can be increased 2–3° C. where the background non-specific binding appears high. A second protocol utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45–50° C.

kd312 nucleic acid molecules, fragments, and/or derivatives that do not themselves encode polypeptides that are active in activity assays may be useful as hybridization probes in diagnostic assays to test, either qualitatively or quantitatively, for the presence of kd312 DNA or RNA in mammalian tissue or bodily fluid samples. kd312 nucleic acid molecules encoding kd312 polypeptides attached to a chimeric polypeptide as described herein above are also included within the scope of this invention.

III. Methods for Preparing kd312 Polypeptides

A. Recombinant Methods

The full length kd312 polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, NY [1994]). A gene or cDNA encoding the kd312 protein or fragment thereof may be obtained for example by screening a genomic or cDNA library, or by PCR amplification. Alternatively, a gene encoding the kd312 polypeptide or fragment may be prepared by chemical synthesis using methods well known to the skilled artisan such as those described by Engels et al.(*Angew. Chem. Intl. Ed.*, 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the kd312 polypeptide will be several hundred nucleotides in length. Nucleic acids larger than about 100 nucleotides can be synthesized as several fragments using these methods. The fragments can then be ligated together to form the full length kd312 polypeptide. Usually, the DNA fragment encoding the amino terminus of the polypeptide will have an ATG, which encodes a methionine residue. This methionine may or may not be present on the mature form of the kd312 polypeptide, depending on whether the polypeptide produced in the host cell is secreted from that cell.

In some cases, it may be desirable to prepare nucleic acid and/or amino acid variants of naturally occurring kd312. Nucleic acid variants (wherein one or more nucleotides are designed to differ from the wild-type or naturally occurring kd312) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce kd312. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site (s) on kd312, or those designed to delete an existing glycosylation and/or phosphorylation site(s) on kd312.

The kd312 gene or cDNA can be inserted into an appropriate expression vector for expression in a host cell. The vector is selected to be functional in the particular host cell employed (i.e., the vector is compatible with the host cell machinery such that amplification of the kd312 gene and/or expression of the gene can occur). The kd312 polypeptide or fragment thereof may be amplified/expressed in prokaryotic, yeast, insect (baculovirus systems) and/or eukaryotic host cells. Selection of the host cell will depend at least in part on whether the kd312 polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the kd312 polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the kd312 coding sequence that encodes polyHis (such as hexaHis) or another small immunogenic sequence. This tag will be expressed along with the protein, and can serve as an affinity tag for purification of the kd312 polypeptide from the host cell. Optionally, the tag can subsequently be removed from the purified kd312 polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native kd312 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the kd312 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the kd312 polypeptide. If the vector of choice does not contain an origin of replication site, one may be chemically synthesized based on a known sequence, and ligated into the vector.

The transcription termination element is typically located 3' of the end of the kd312 polypeptide coding sequence and serves to terminate transcription of the kd312 polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the kd312 polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In many cases, transcription of the kd312 polypeptide is increased by the presence of one or more introns on the vector; this is particularly true where kd312 is produced in eukaryotic host cells, especially mammalian host cells. The introns used may be naturally occurring within the kd312 nucleic acid sequence, especially where the kd312 sequence used is a full length genomic sequence or a fragment thereof. Where the intron is not naturally occurring within the kd312 DNA sequence (as for most cDNAs), the intron(s) may be obtained from another source. The position of the intron with respect to the 5' flanking sequence and the kd312 coding sequence is important, as the intron must be transcribed to be effective. As such, where the kd312 nucleic acid sequence is a cDNA sequence, the preferred position for the intron is 3' to the transcription start site, and 5' to the polyA transcription termination sequence. Preferably for kd312 cDNAs, the intron will be located on one side or the other (i.e., 5' or 3') of the kd312 coding sequence such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vector such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and/or mammalian host cells. Such vectors include, inter alia, PCRII (Invitrogen Company, San Diego, Calif., PBSII (Stratagene Company, Lajolla, Calif.), and pETL (BlueBacII; Invitrogen).

After the vector has been constructed and a kd312 nucleic acid has been inserted into the proper site of the vector, the completed vector may be inserted into a suitable host cell for amplification and/or kd312 polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize kd312 protein which can subsequently be collected from the culture medium (if the host cell secretes it into the medium) or directly from the host cell producing it (if it is not secreted). After collection, the kd312 protein can be purified using methods such as molecular sieve chromatography, affinity chromatography, and the like.

Selection of the host cell will depend in part on whether the kd312 protein is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize biologically active kd312, the kd312 may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, DH12S and MC1061) are well-known as host cells in the field of biotechnology. Various strains of *B. subtilis*, Pseudomonas spp., other Bacillus spp., Strept oomyces spp., and the like may also be employed in this method.

Many strains of yeast cells known to those skilled in the art are also available as host cells for expression of the polypeptides of the present invention. Additionally, where desired, insect cells may be utilized as host cells in the method of the present invention (Miller et al., *Genetic Engineering* 8: 277–298 [1986]).

Insertion (also referred to as "transformation" or "transfection") of the vector into the selected host cell may be accomplished using such methods as calcium phosphate, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of kd312 polypeptide produced in the host cell can be evaluated using standard methods known in the art. Such methods include, without limitation, Western blot analysis, SDS-polyacrylamide gel electrophoresis, nondenaturing gel electrophoresis, HPLC separation, immunoprecipitation, and/or activity assays such as kinase assays.

If the kd312 polypeptide has been designed to be secreted from the host cells, the majority of polypeptide may be found in the cell culture medium. Polypeptides prepared in this way will typically not possess an amino terminal methionine, as it is removed during secretion from the cell. If however, the kd312 polypeptide is not secreted from the host cells, it will be present in the cytoplasm (for eukaryotic, gram positive bacteria, and insect host cells) or in the periplasm (for gram negative bacteria host cells) and may have an amino terminal methionine.

For intracellular kd312 protein, the host cells are typically first disrupted mechanically or osmotically to release the cytoplasmic contents into a buffered solution. kd312 polypeptide can then be isolated from this solution.

Purification of kd312 polypeptide from solution can be accomplished using a variety of techniques. If the polypeptide has been synthesized such that it contains a tag such as Hexahistidine (kd312/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing kd312). For example, polyhistidine binds with great affinity and specificity to nickel, thus an affinity column of nickel (such as the Qiagen nickel columns) can be used for purification of kd312/polyHis. (See for example, Ausubel et al., eds., *Current Protocols in Molecular Biology*, Section 10.11.8, John Wiley & Sons, New York [1993]).

Where the kd312 polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

If it is anticipated that the kd312 polypeptide will be found primarily in the periplasmic space of the bacteria or the cytoplasm of eukaryotic cells, the contents of the periplasm or cytoplasm, including inclusion bodies (e.g., gram-negative bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the kd312 polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The kd312 polypeptide in its now soluble form can then be analyzed using gel electrophoresis, immunoprecipitation or the like. If it is desired to isolate the kd312 polypeptide, isolation may be accomplished using standard methods such as those set forth below and in Marston et al. (*Meth. Enz.*, 182:264–275 [1990]).

If kd312 polypeptide inclusion bodies are not formed to a significant degree in the periplasm of the host cell, the kd312 polypeptide will be found primarily in the supernatant after centrifugation of the cell homogenate, and the kd312 polypeptide can be isolated from the supernatant using methods such as those set forth below.

In those situations where it is preferable to partially or completely isolate the kd312 polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

B. Chemical Synthesis Methods

In addition to preparing and purifying kd312 polypeptide using recombinant DNA techniques, the kd312 polypeptides, fragments, and/or derivatives thereof may be prepared by chemical synthesis methods (such as solid phase peptide synthesis) using methods known in the art such as those set forth by Merrifield et al., (*J. Am. Chem. Soc.*, 85:2149 [1964]), Houghten et al. (*Proc Natl Acad. Sci. USA*, 82:5132 [1985]), and Stewart and Young (Solid Phase Peptide Synthesis, Pierce Chem Co, Rockford, Ill. [1984]). Such polypeptides may be synthesized with or without a methionine on the amino terminus. Chemically synthesized kd312 polypeptides or fragments may be oxidized using methods set forth in these references to form disulfide bridges. The kd312 polypeptides or fragments may be employed as biologically active or immunological substitutes for natural, purified kd312 polypeptides in therapeutic and immunological processes.

IV. Chemically Modified kd312 Derivatives

Chemically modified kd312 compositions (i.e., "derivatives") where the kd312 polypeptide is linked to a polymer ("kd312-polymers") are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of kd312-polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1–C10 alkoxy or aryloxy derivatives thereof (see U.S. Pat. No. 5,252,714).

Pegylation of kd312 may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable conditions used to react a biologically active substance with an activated polymer molecule. Methods for preparing pegylated kd312 will generally comprise the steps of (a) reacting a kd312 polypeptide with polyethylene glycol (such as a reactive ester or aldehyde derivative of PEG) under conditions whereby kd312 becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of polypegylated product.

Generally, conditions which may be alleviated or modulated by administration of the present polymer/kd312 include those described herein for kd312 molecules in general. However, the polymer/kd312 molecules disclosed herein may have additional activities, enhanced or reduced activities, or other characteristics, as compared to the non-derivatized molecules.

V. Combinations

The kd312 polypeptides and fragments thereof, whether or not chemically modified, may be employed alone, or in combination with other pharmaceutical compositions such as, for example, cytokines, interferons, interleukins, growth factors, antibiotics, anti-inflammatories, chemotherapeutic agents, in the treatment of various disorders, such as cancer, immunodeficiency, and neurodegeneration.

VI. Antibodies

The kd312 polypeptides, fragments, and/or derivatives thereof may be used to prepare antibodies generated by standard methods. Thus, antibodies that react with the kd312 polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will be "humanized", i.e., prepared so as to prevent or minimize an immune reaction to the antibody when administered to a patient. The antibody fragment may be any fragment that is reactive with the kd312 of the present invention, such as, $F_{ab}$, $F_{ab}'$, etc. Also provided by this invention are the hybridomas generated by presenting kd312 or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human kd312 polypeptide of the present invention are also encompassed by this invention.

The antibodies may be used therapeutically, such as to inhibit binding of kd312 to its substrates. The antibodies may further be used for in vivo and in vitro diagnostic purposes, such as in labeled form to detect the presence of the kd312 polypeptide in a tissue.

Antibodies against kd312-1, particularly human, and active fragments thereof, are preferred.

VII. Therapeutic Compositions and Administration Thereof

As used herein, the terms "effective amount" and "therapeutically effective amount" refer to the amount of kd312 necessary to support one or more biological activities of kd312 as set forth herein.

Therapeutic compositions for treating various disorders or diseases associated with cell death are within the scope of the present invention.

Such compositions may comprise a therapeutically effective amount of a kd312 polypeptide, a fragment thereof (either of which may be chemically modified) or a modulator of kd312 activity, (collectively, a "kd312 therapeutic compound") in admixture with a pharmaceutically acceptable carrier. The carrier material may be water for injection, preferably supplemented with other materials common in solutions for administration to mammals. Typically, a kd312 therapeutic compound will be administered in the form of a composition comprising the kd312 therapeutic compound in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. An exemplary composition comprises citrate buffer of about pH 4.0–4.5, which may further include NaCl.

The kd312 compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of kd312 compositions useful for practicing the present invention may be prepared for storage by mixing the selected composition having the desired degree of purity with optional physiologically acceptable carriers, excipients, or stabilizers (*Remington's Pharmaceutical Sciences*, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The kd312 composition to be used for in vivo administration must be sterile. This is readily accomplished by filtration through sterile filtration membranes. Where the kd312 composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, kd312 may be administered locally via implantation into the affected area of a membrane, sponge, or other appropriate material on to which kd312 polypeptide has been absorbed.

Where an implantation device is used, the device may be implanted into any suitable tissue or organ, such as, for example, into a cerebral ventricle or into brain parenchyma, and delivery of kd312 may be directly through the device via bolus or continuous administration, or via a catheter using continuous infusion.

kd312 polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamine (Sidman et al, *Biopolymers,* 22: 547–556 [1983]), poly(2-hydroxyethyl-methacrylate) (Langer et al., *J. Biomed. Mater. Res.,* 15: 167–277 [1981] and Langer, *Chem. Tech.,* 12: 98–105 [1982]), ethylene vinyl acetate (Langer et al., supra) or poly-D(–)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA,* 82: 3688–3692 [1985]; Hwang et al., *Proc. Natl. Acad. Sci. USA,* 77: 4030–4034 [1980]; EP 52,322; EP 36,676; EP 88,046; EP 143,949).

In some cases, it may be desirable to use kd312 compositions in an ex vivo manner, i.e., to treat cells or tissues that have been removed from the patient and are then subsequently implanted back into the patient.

In other cases, kd312 may be delivered through implanting into patients certain cells that have been genetically engineered to express and secrete kd312 polypeptide. Such cells may be animal or human cells, and may be derived from the patient's own tissue or from another source, either human or non-human. Optionally, the cells may be immortalized. The cells may be implanted into the brain, adrenal gland or into other suitable body tissues or organs of the patient.

In certain situations, it may be desirable to use gene therapy methods for administration of kd312 to patients suffering from certain (e.g., neurological, immunological, and other) disorders. In these situations, genomic DNA, cDNA, and/or synthetic DNA encoding kd312 or a fragment or variant thereof may be operably linked to a constitutive or inducible promoter that is active in the tissue into which the composition will be injected. This kd312 DNA construct, either inserted into a vector, or alone without a vector, can be injected or otherwise administered directly into brain, heart, or other tissue, either neuronal or non-neuronal.

An effective amount of the kd312 composition(s) to be employed therapeutically will depend, for example, upon the therapeutic objectives such as the indication for which kd312 is being used, the route of administration, and the condition of the patient. Accordingly, it will be necessary for the therapist to titer the dosage and modify the route of administration as required to obtain the optimal therapeutic effect. A typical daily dosage may range from about 0.1 $\mu$g/kg to up to 10 mg/kg or more, depending on the factors mentioned above. Typically, a clinician will administer the kd312 composition until a dosage is reached that achieves the desired effect. The kd312 composition may therefore be administered as a single dose, or as two or more doses (which may or may not contain the same amount of kd312) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

VIII. Diagnostic Uses kd312 RNA and protein levels may be measured for diagnostic purposes. Such levels may be indicative of the presence or progression of various diseases, such as cancer, immunodeficiency disorders (e.g., AIDS), stroke, heart attack, head trauma, and neurodegenerative diseases (e.g., Parkinson's disease and Alzheimer's disease), preferably cancer.

IX. Conditions to Be Treated with kd312

The kd312 proteins, fragments and/or derivatives thereof may be utilized to treat diseases and disorders associated with alterations in cell proliferation/death which may benefit from exposure to kd312 or anti-kd312 antibodies. kd312 protein and/or fragments or derivatives thereof, may be used directly to treat patients suffering from cancer, immunodeficiency disorders (e.g., AIDS), stroke, heart attack, head trauma, and neurodegenerative diseases (e.g., Parkinson's disease and Alzheimer's disease).

X. Modulators of kd312 Levels

In some situations, such as treatment of cancer, it may be desirable to inhibit or significantly decrease the level of kd312 activity or expression. Compounds that inhibit kd312 activity/expression could be administered either in an ex vivo manner, or in an in vivo manner by local or iv injection, or by oral delivery, implantation device, or the like. Exemplary inhibitory compounds are antisense oligonucleotides against kd312 genes, antibodies against kd312 proteins, and small molecule inhibitors of kd312 expression or activity.

In other situations, such as in cases wherein cell survival is desirably increased (e.g., AIDS, stroke, neurodegenerative diseases, head/brain trauma, and heart attack, etc.), it may be desirable to enhance or significantly increase the level of kd312 activity or expression. Compounds that increase kd312 activity or expression could be administered either in an ex vivo manner, or in an in vivo manner by local or iv injection, or by oral delivery, implantation device, or the like.

The assays described below provide examples of methods useful for identifying compounds that could inhibit or enhance kd312 activity.

For ease of reading, the following definition is used herein for describing the assays:

"Test molecule(s)" refers to the molecule(s) that is under evaluation as a modulator of kd312, e.g., by virtue of its potential ability to block or enhance the kinase activity of kd312.

Several types of in vitro assays using purified protein may be conducted to identify those compounds that affect kd312 function. Such affect may be accomplished by a compound that typically inhibits or enhances the activity or expression level of kd312.

Two easily-performed assays can be used to screen test molecules for inducers or inhibitors of genomic kd312.

1. RT-PCR can be performed to estimate the level of kd312 message in cells normally expressing kd312 in the presence and absence of various test molecules.

2. A reporter gene can be fused to genomic kd312 and the fusion gene can then be cloned into a vector and introduced into cells normally expressing kd312. The activities of the reporter protein can be measured to estimate expression levels of kd312 in response to a test molecule.

For example, a fusion gene between rat genomic kd312 and firefly luciferase gene has been constructed for this purpose since a luciferase assay system is commercially available (PROMEGA) and is sensitive and accurate. In this construct the kd312 coding region for the membrane-targeting CAAX domain was deleted to ensure that the luciferase protein is freely available inside the cells for detection. The coding region of rat KD12 between the triplet ATG specifying the initiating codon for translation and the SacII restriction site within the first exon was replaced in frame with the entire coding region of the firefly luciferase gene. The nucleotide sequences potentially important for the regulation of kd312, including sequences flanking transcribed region at 5' and 3'-end and the sequence of the single intron, are completely unaltered in the fusion gene.

Typically, the test molecule will be tested over a range of concentrations, and a series of controls lacking one or more elements of the test assays can be used for accuracy in evaluating the results.

In some cases, it may be desirable to evaluate two or more test molecules together for use in decreasing or increasing kd312 activity. In these cases, the assays set forth above can be readily modified by adding such additional test molecule (s) either simultaneously with, or subsequently to, the first test molecule. The remainder of steps in the assay can be as set forth above.

XI. Transgenic Mammals

Also included within the scope of the present invention are non-human mammals such as mice, rats, rabbits, goats, or sheep in which the gene (or genes) encoding the human equivalent of kd312 (e.g., kd312-1) has been disrupted ("knocked out") such that the level of expression of this gene is significantly decreased or completely abolished. Such mammals may be prepared using techniques and methods such as those described in U.S. Pat. No. 5,557,032. The present invention further includes non-human mammals such as mice, rats, rabbits, goats, or sheep in which the gene (or genes) encoding the kd312 (either the native form of kd312 for the mammal or a heterologous kd312 gene) is over expressed by the mammal, thereby creating a "transgenic" mammal. Such transgenic mammals may be prepared using well known methods such as those described in U.S. Pat. No 5,489,743 and PCT patent application no. WO94/28122, published Dec. 8, 1994.

The following examples are intended for illustration purposes only, and should not be construed as limiting the scope of the invention in any way.

EXAMPLES

Example 1

Animal Experiments

Blood was removed from Sprague-Dawley rats by cardiac puncture at 0, 3, and 8 hr. Immediately after each blood removal, the animals were injected with an equal volume of 0.9% NaCl to prevent hypovolumic shock. Three hours after the final blood removal a small blood sample was taken and the hematocrit reading was determined. The animals were then sacrificed and internal organs were removed for future experiments. Organ samples were also obtained from normal animals for control experiments.

Molecular Biology

Total RNA and polyA$^+$ RNA were isolated using Fast-track isolation kits from Invitrogen corporation. cDNA libraries were constructed in plasmid pSPORT 1 (for polyA$^+$ RNA from rats with blood loss) and in plasmid pSPORT 2 (for poly$^+$A RNA from normal rats) using the GIBCO BRL SuperScript™ Plasmid System for cDNA Synthesis and Plasmid Cloning. Subtractive hybridization to find bleeding-induced genes from rat kidneys was performed according to Gruber et al, 1993, Focus 15, Number 3, pp. 59–65. After two rounds of subtractive hybridization individual colonies were pooled and their DNA was isolated and analyzed on agarose gel. A major contaminating band was found on gel and was identified to be a deletion product of the vector pSPORT1 after determination of its nucleotide sequence. Circular DNA larger than the contaminating molecule was extracted from the gel and was used in the transformation of the *E.coli* host DH12S (GIBCO BRL) to constract a sub-tracted library. Individual colonies from this library were screened for bleeding-induced genes by DNA sequencing on each plasmid isolate and RT-PCR on polyA$^+$ RNA from kidneys of normal rats and rats with severe blood loss based on the nucleotide sequences of the inserts in the plasmids. The bleeding-induced nature of each candidate gene was confirmed by Northern analysis. Nucleotide sequences of all clones derived in this project were determined by the sequencing group at Amgen. RT-PCR was performed by using the SuperScript Preamplification System for First Strand cDNA Synthesis from GIBCO BRL and the PCR core kit from Boehringer Mannheim. Oligonucleotides were synthesized by Amgen-Boulder. Northern analysis was performed by using the NorthernMax Northern blotting kit from Ambion.

The rat kd312 cDNA orignally isolated after subtractive hybridization lacked its 5'-end (encoding 232 of 280 amino acids). The 5'-end of the molecule was obtained by using the 5' RACE System for Rapid Amplification of cDNA Ends from Gibco BRL and was assembled with the 3'-portion of the molecule. A human kd312 gene fragment of ~500 base pairs was isolated from cDNA synthesized from human brain polyA+ RNA using the method of 5' RACE and a primer of rat kd312 sequence. Based on the nucleotide sequence of this fragment and the published nuleotide sequence of R-ras gene, the human kd312 and R-ras biotinylated oligonucleotide probes (18–22 bases) were synthesized and the full-length human kd312 and R-ras cDNA molecules were isolated from a human kidney cDNA library (Gibco BRL) by using the Gene Trapper cDNA Positive Selection System from Gibco BRL. Human and rat kd312 genomic DNA were isolated from a human placenta EMBL3 library (Clontech) and a Sprague-Dawley rat liver EMBL3 library (Clontech) by the method of plaque hybridization according to Sambrook et al (1989). In this experiment human and rat kd312 cDNA were used as templates to synthesize $^{32}$P-labelled probes with Amersham $^{32}$P-dCTP labelling system.

Example 2

Figure 11:
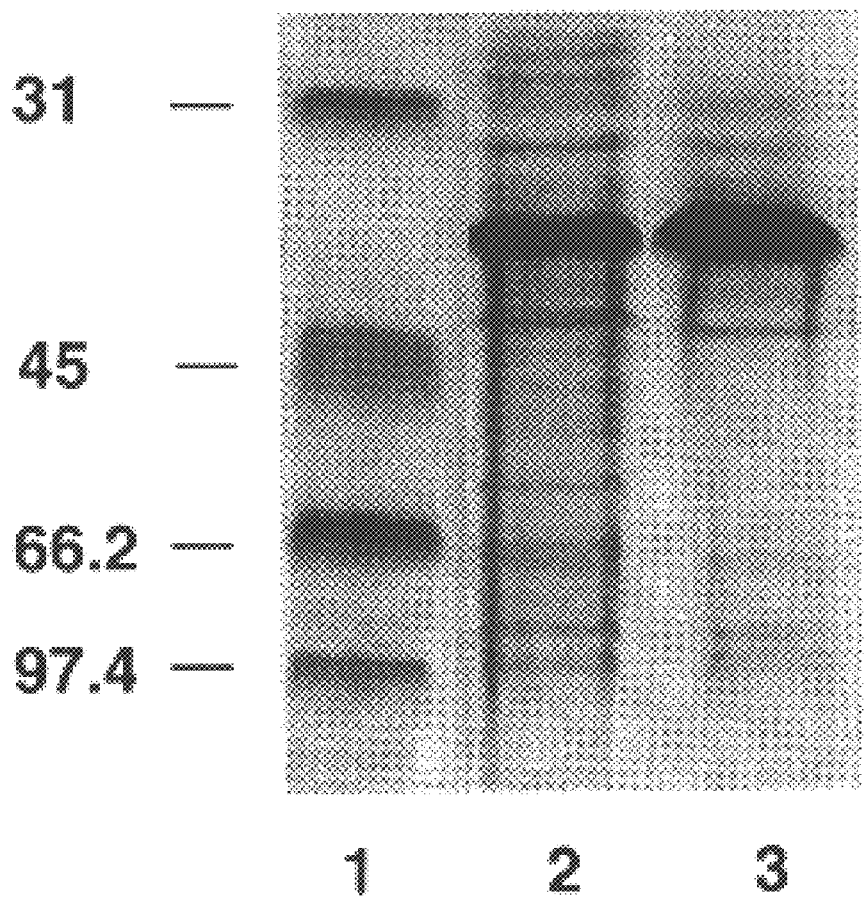
FIG. 11 shows SDS-PAGE analysis of human kd312 protein produced in *E. coli*. Human kd312 gene was expressed from the vector pET-30a(+)-2 and the kd312 protein was partially purified from *E. coli* cells using Novagen His-Bind Resin as described in the Examples section. Conditions for SDS-PAGE analysis was essentially the same as described in connection with Western analysis. Cell lysates were prepared from 400 ml induced cells ($OD_{600}$=0.6) and the kd312 protein was eluted from the His-Bind Resin in 12 ml elution buffer according to the protocol supplied by Novagen. In lane 2, 25 μl cell lysates, and in lane 3, 5 μl protein elute. from the His-Bind Resin were loaded on the gel. Lane 1 is molecular weight standard purchased from BIO-RAD.
Figure 12:
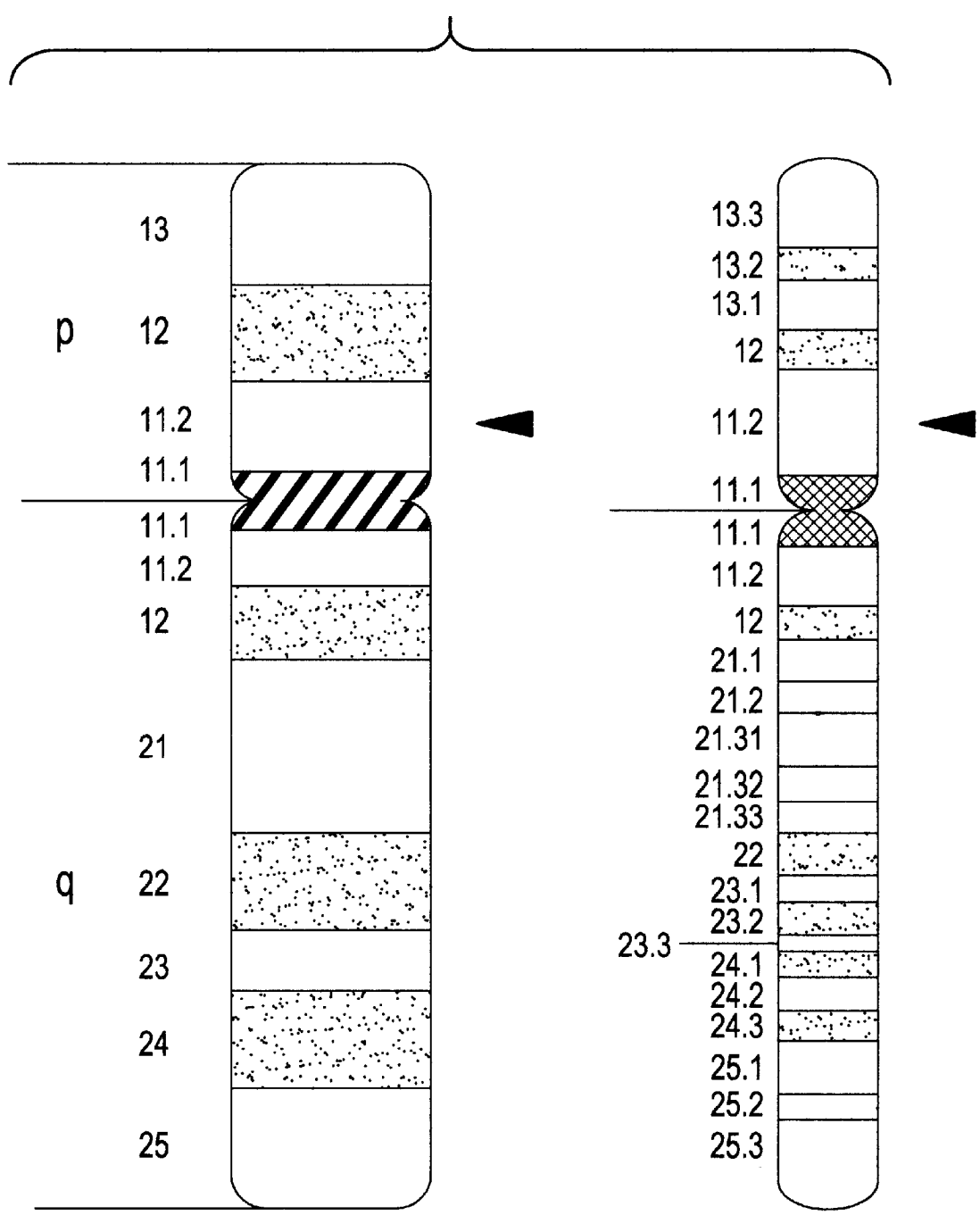
FIG. 12 shows two ideograms illustrating the chromosomal position of human kd312 gene at 17p11.2 (See Examples). Both ideograms are from the International System for Human Cytogenetic Nomenclature (1995).

Both human and rat kd312 cDNA were expressed in *E. coli* and in the human embryonic cell line 293. See FIGS. 10 and 11. The pET expression vectors (purchased from Novagen), in which gene expression is controlled by strong bacteriophage T7 transcription and translation signals, were used for the expression of kd312 cDNA in *E.coli*. An additional expression vector, pET-30a(+)-2, suitable for this purpose was constructed from the commercially purchased vector pET-30a(+) (from Novagen). The NdeI restriction site in the expression vector pET-30a(+) was removed by cutting with NdeI followed by end-filling and ligating the ends. The NcoI site in the resulting molecule was then replaced with an NdeI site by replacing the small Asp718-BamHI fragment with a synthetic oligonucleotide with appropriate base changes to construct pET-30a(+)-2. The 5'-most trinucleotide ATG and its upstream adjoining trinucleotide within both human and rat kd312 coding regions were converted into an NdeI site with similar procedures and the coding sequences of both human and rat kd312 cDNA from the NdeI site were cloned into the NdeI and another downstream cloning site of pET-30a(+)-2 for expression. This construction fused kd312 coding sequence at the 5'-end with two short sequences encoding S-tag and His-tag respectively. Both tags make it possible to purify kd312 protein in one step using affinity resins. The NdeI-bearing human and rat kd312 cDNA were also fused to coding sequences for S-tag, His-tag, and *E.coli* thioredoxin protein in the vector pET-32a(+) and expressed as a fusion protein.

The recombinant constructs were introduced into a λDE3 lysogen of *E. coli* strain BL21 by transformation and the resulting strains were grown at 30° C. and induced with IPTG in LB for 3 hours according to the protocol supplied by Novagen. kd312 proteins expressed from both systems were purified in milligram quantities under denaturing conditions in the presence of 6M urea using His-Bind Resin, His-Bind Buffer Kit and the protocol supplied by Novagen.

The human kd312 protein carring S-tag and His-tag was used in the generation of antiserum against kd312 protein in rats. To express kd312 proteins in mammalian cells both human and rat kd312 cDNA were cloned into the multiple cloning site of the episomal mammalian expression vector pCEP4 (Invitrogen) and the resulting plasmids were introduced into the 293 cells for constitutive expression of the kd312 gene from the cytomegalovirus (CMV) immediate early enhancer/promoter. Expression of kd312 proteins were confirmed by Western Blotting which was performed according to the protocol supplied by Pierce Chemical Company. In these experiments cell lysates were prepared by sonicating cells in 6M urea in Tris buffer (pH7.5, 20 mM) for 10–20 seconds after washing the cells in Dulbecco's phosphate-buffered saline (GibcoBRL). Cell lysates and equal volume (15 μl) of loading buffer (50 mM Tris-Cl,pH 6.8, 100 mM dithiothreitol, 2% SDS, 0.1% bromophenol blue, 10% glycerol) were heated at 100° C. for 5 minutes and the mixture was loaded on 12% polyacrylamide gel for protein separation and blotting. The anti-kd312 antiserum was diluted 500 fold and the HRP-labeled goat anti-rat IgG antibody (Pierce) was diluted 5000 fold before use.

Transfections of 293 cells with the plasmid pCEP4 or its derivatives were performed by using LipofectAMINE Reagent and the protocol supplied with it by Gibco BRL. Transfected cells were grown in Gibco BRL D-MEM high-glucose medium that lacked sodium pyruvate and was supplemented with 10% FBS and 300 μg/ml hygromycin. Fluorescence-activated cell sorting (FACS) for apoptosis assays was performed according to Polverino and Patterson, J. Biol. Chem. 272, No. 11: 7013–7021 (1997).

Example 3

Chromosomal Localization of Clone F457 by Fluorescene In Situ Hybridization

DNA from ATCC 98666 was labeled with digoxigenin dUTP by nick translation. Labeled probe was combined with sheared human DNA and hybridized to normal metaphase chromosomes derived from PHA stimulated peripheral blood lymphocytes in a solution containing 50% formamide, 10% dextran sulfate and 2×SSC. Specific hybridization signals were detected by incubating the hybridized slides in fluoresceinated antidigoxigenin antibodies followed by counterstaining with DAPI. The initial experiment resulted in specific labeling of the proximal short arm of a group E chromosome which was believed to be chromosome 17 on the basis of size, morphology, and banding pattern. A second experiment was conducted in which a genomic probe which has been previously mapped to the long arm of chromosome 17 and confirmed by cohybridization with a chromosome 17 centromere probe was cohybridized with clone F457. This experiment resulted in the specific lableing of the distal long arm and the short arm of chromosome 17. Measurements of 10 specifically labeled chromosomes 17 demonstrated that DNA from ATCC 98666 is located at a position which is 16% of the distance from the centromere to the telomere of chromosome arm 17p, an area which corresponds to band 17p11.2. A total of 80 metaphase cells were analyzed with 41 exhibiting specific labeling.

Discussion

A novel blood loss-induced gene, kd312, was isolated from a cDNA library prepared from the kidneys of Sprague-Dawley rats recovering from severe blood loss by subtractive hybridization. A major volume (~60%) of blood was first removed from the rats by heart puncture and replaced with saline. The kidneys and other organs were then removed several hours after the operation from the animals which were recovering from the blood loss. PolyA+ RNAs were isolated from the kidneys as well as kidneys of normal animals and were converted into complementary DNA (cDNA). DNA sequences common to both cDNA populations were removed by the technique of subtractive hybridization. It involved preparation of biotinylated RNA driver, hybridization with single-stranded cDNA target, binding of streptavidin, and removal of RNA-DNA hybrids by phenol extraction. The remaining unhybridized cDNA was converted into a double-stranded cDNA library and the library was screened for bleeding-induced genes. Partial DNA sequences of individual clones were determined and bleeding-induced sequences were identified by RT-PCR on polyA$^+$ RNA from normal and anemic animals. Over 400 clones were screened from a cDNA library derived from a rat which was sacrificed 8 hours after operation when the hematocrit reading was 39% of normal level. A partial cDNA molecule lacking the 5'-end was identified as a highly induced gene (designated kd312) after severe blood loss. The 5'-end of kd312 cDNA was isolated by the method of 5' RACE (Rapid Amplification of cDNA Ends).

Figure 1B:
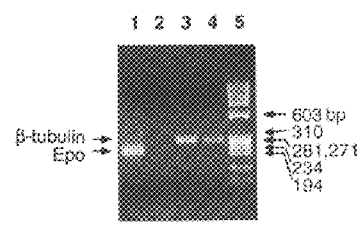

The blood loss-induced nature of kd312 was confirmed by Northern blotting experiments. To prevent cross hybridization with related sequences a kd312 cDNA fragment (391 base pairs) corresponding to a 3' untranslated region was used to probe total RNA prepared from the kidneys of the animal which gave rise to kd312 and also the kidneys of a normal animal. As a comparison the same RNA preparations were also analyzed by RT-PCR for the presence of Epo message. As shown in FIG. 1 both kd312 and Epo messages were highly induced when the animal was recovering from severe blood loss. Neither message was detectable in the kidneys of the normal animal. The same results were obtained on RNAs prepared from different animals suffering blood loss (data not shown). In addition, kd312 was induced in the livers and thymuses of the same anemic rats tested (data not shown).

The human homolog of kd312 was isolated from a kidney cDNA library. Comparison of the deduced amino acid sequences of rat and human kd312 proteins indicates that this protein is well conserved between rats and humans (FIG. 2). The rat kd312 protein (280 amino acids) shares 97.5% identity with that of the human counterpart (281 amino acids). GenBank and EMBL search revealed that the kd312 protein is distantly related to the Ras protein faimily. The human kd312 is most homologous with the R-Ras member of the human Ras family and shares 33.8% amino acids sequence identity with human R-Ras (FIG. 3). Similar to Ras proteins, kd312 carries a GTP-binding site close to the amino terminus and a CAAX motif for membrane-targeting at the C-terminus (FIG. 2). These features suggest that kd312 functions as a GTP-dependent membrane protein.

The function of kd312 was first investigated by testing its ability to transform cells in vitro and its ability to promote or inhibit apoptosis. Transformation of NIH373 cells following expression of the kd312 gene was tested. Under the experimental conditions, expression of the murine H-ras gene (v-ras or c-ras) but not the human or rat kd312 from the vector pEV7 led to focus formation in NIH3T3 cells.

Figure 4:
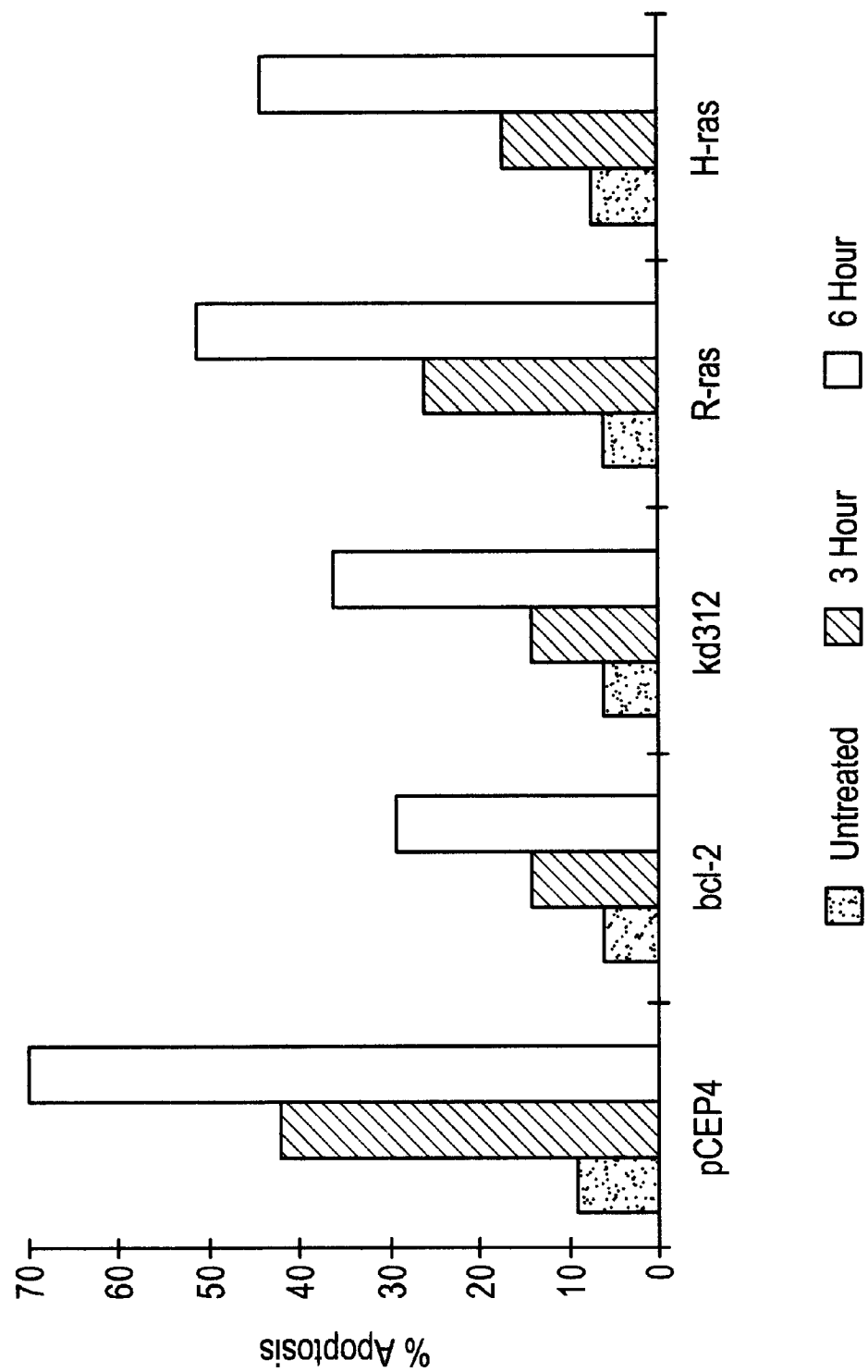
FIG. 4 depicts inhibition of apoptosis by human kd312 as compared to other proteins (as indicated). Shown graphs are the results from FACS analysis of apoptosis induced by geranylgeraniol in 293 cells transfected with various genes. Cells were treated with 10 µM geranylgeraniol for various times as indicated. Subsequently, the cells were washed and stained with 50 µg/ml propidium iodide in 3.8 mM sodium citrate pH 7.0 and analyzed using a FACScan flow cytometer. The extent of apoptosis was determined by measuring the proportion of cells displaying hypo-diploid DNA content. The data represent the average of 2 independent experiments.

Involvement of kd312 in apoptosis was tested in the human embryonal kidney cell line 293 following expression of this gene from the episomal expression vector pCEP4. Derivatives of 293 cells constitutively expressing human kd312, bcl-2, R-ras, and murine H-ras genes from pCEP4 were established. Expression of each gene was confirmed by Western blotting experiments (data not shown). A cell line expressing the murine bax gene could not be established and expression of this gene in 293 cells invariably led to cell death. As shown in FIG. 4, expression of kd312 protected 293 cells from geranylgeraniol-induced apoptosis as well as did expression of bcl-2 which encodes a potent apoptosis inhibitor. It has been shown that R-ras promotes apoptosis following expression in 32, D3, FL5.12, and NIH3T3 cells. However, expression of R-ras or H-ras in 293 cells inhibited apoptosis (FIG. 4). The levels of inhibition following expression of the ras genes, particularly R-ras, were unmistakably lower than those resulting from the expression of kd312.

To define the way that kd312 exerts its function we have tested its interaction with human Raf, H-Ras, and bcl-2 using a yeast two-hybrid system. No interaction between kd312 and any of these proteins was detected. Work is in progress to search for kd312 interacting proteins using the same yeast system.

As a first step to find the kd312 inducer, we have isolated human kd312 genomic DNA from a human placenta genomic library and determined its nucleotide sequence. The kd312 gene consists of two exons separated by a single intron of 211 base paris (FIG. 5). Just upstream of the kd312 coding region and within the transcribed region, two short sequences which share significant homology with a promoter region of the human erythropoietin gene (Epo) essential for a portion of hypoxia-induction were identified (FIG. 5 and 6). Further upstream, a TATA box and a binding site for the transcription factor SP1, none of which is present in the Epo promoter region, were identified (FIG. 5). No binding site for the hypoxia-inducible factor 1 (HIF-1) can be recognized either upstream or downstream of the kd312 coding region.

We have isolated a novel gene kd312 and showed that this gene is highly induced in vivo as is the Epo gene after severe blood loss. It is likely that enhanced synthesis of kd312 protein, like erythropoietin, helps human bodies survive severe stress such as massive blood loss. We have demonstrated that kd312 protects 293 cells from chemical-induced apoptosis.

kd312 contains a CAAX motif and functions most likely as a membrane protein. Inducers or inhibitors of kd312 as well as proteins that interact with kd312 are candidates for pharmaceutical products or therapeutic targets.

Deposit of DNA

The following *E. coli* cells have been deposited with the ATCC (American Type Culture Collection, 12301 Parklawn Drive, Rockville, Md., USA) on Feb. 19, 1998 and assigned the indicated accession numbers:

|  | ATCC No. |
|---|---|
| *E. coli* strain SCS110 carrying plasmid pRkd312, EcY534 | 98664 |
| *E. coli* strain SCS110 carrying plasmid pHkd312, EcY5441 | 98665 |
| *E. coli* strain HB101 carrying plasmid PHkd312G, EcY5545 | 98666 |
| *E. coli* strain DH12S carrying plasmid pRkd312G, EcY5602 | 98667 |

What is claimed is:

1. A kd312 polypeptide that consists of amino acids 6–281 of SEQ ID NO:2.

2. A kd312 polypeptide that consists of amino acids 10–281 of SEQ ID NO:2.

3. A kd312 polypeptide that consists of amino acids 6–280 of SEQ ID NO:5.

4. A kd312 polypeptide that consists of amino acids 10–280 of SEQ ID NO:5.

5. A kd312 polypeptide having anti-apoptotic activity selected from the group consisting of:
    (a) the polypeptide of SEQ ID NO:2;
    (b) a polypeptide which has the same number and sequence of amino acids as (a) except for having from 1 to 14 conservative amino acid substitutions therein and which has said anti-apoptotic activity; and
    (c) a polypeptide fragment of (a) or (b) which has said anti-apoptotic activity.

6. A kd312 polypeptide having anti-apoptotic activity selected from the group consisting of:
    (a) the polypeptide of SEQ ID NO:5;
    (b) a polypeptide which has the same number and sequence of amino acids as (a) except for having from 1 to 14 conservative amino acid substitutions therein and which has said anti-apoptotic activity; and
    (c) a polypeptide fragment of (a) or (b) which has said anti-apoptotic activity.

\* \* \* \* \*